US009222874B2

(12) United States Patent
Hill et al.

(10) Patent No.: US 9,222,874 B2
(45) Date of Patent: Dec. 29, 2015

(54) SYSTEMS AND METHODS FOR INDIVIDUALLY TRAPPING PARTICLES FROM AIR AND MEASURING THE OPTICAL SPECTRA OR OTHER PROPERTIES OF INDIVIDUAL TRAPPED PARTICLES

(71) Applicant: U.S. Army Research Laboratory ATTN: RDRL-LOC-I, Adelphi, MD (US)

(72) Inventors: Steven C. Hill, Silver Spring, MD (US); Yongle Pan, Cheshire, CT (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 173 days.

(21) Appl. No.: 13/793,556

(22) Filed: Mar. 11, 2013

(65) Prior Publication Data

US 2014/0004559 A1 Jan. 2, 2014

Related U.S. Application Data

(60) Provisional application No. 61/665,031, filed on Jun. 27, 2012.

(51) Int. Cl.
*G01N 21/01* (2006.01)
*G01N 21/65* (2006.01)
*G01N 15/14* (2006.01)

(52) U.S. Cl.
CPC ............. *G01N 21/01* (2013.01); *G01N 15/14* (2013.01); *G01N 21/65* (2013.01)

(58) Field of Classification Search
CPC . G01N 1/2202; G01N 1/2001; G01N 1/2223; G01N 21/6402; G01N 21/65; G01N 2015/149; G01N 2015/1081; G01N 15/1434; G01N 1/2273
USPC .......... 209/552, 576–579, 586–589; 700/219, 700/223; 422/509; 435/228.7; 356/301–303; 250/251, 282, 339.11
See application file for complete search history.

(56) References Cited

U.S. PATENT DOCUMENTS

| 5,689,333 | A | * | 11/1997 | Batchelder et al. ........... 356/301 |
| 5,866,430 | A | * | 2/1999 | Grow ................................ 506/6 |
| 6,532,067 | B1 | | 3/2003 | Chang et al. |
| 6,947,134 | B2 | | 9/2005 | Chang et al. |

(Continued)

OTHER PUBLICATIONS

Alexander, T. A., P. M. Pellegrino, and J. B. Gillespie, "Near-infrared surface-enhanced-Raman-scattering-mediated detection of single optically trapped bacterial spores," Applied Spectroscopy 54, 1340-1345 (2003).

(Continued)

*Primary Examiner* — Joseph C Rodriguez
(74) *Attorney, Agent, or Firm* — Eric Brett Compton

(57) ABSTRACT

Embodiments of the present invention are directed to systems and methods for continuously sampling particles from air. In one embodiment, a system for continuously sampling particles from air may include: an airflow system configured to continuously draw air including airborne particles into the system; a photophoretic trap that uses photophoretic forces of a laser beam to trap one or more of the airborne particles from the drawn air; a measurement device configured to measure one or more properties of the trapped one or more airborne particles; and a controller configured to repeatedly trap, measure and release one or more airborne particles.

26 Claims, 16 Drawing Sheets

(56) References Cited

U.S. PATENT DOCUMENTS

| | | | |
|---|---|---|---|
| 7,126,687 B2 | 10/2006 | Hill et al. | |
| 7,262,840 B2 | 8/2007 | Maier et al. | |
| 7,410,063 B1 | 8/2008 | Chang et al. | |
| 8,140,300 B2* | 3/2012 | Dunne et al. | 702/186 |
| 8,263,023 B2* | 9/2012 | Le Vot et al. | 422/503 |
| 8,395,769 B2* | 3/2013 | Stewart et al. | 356/301 |
| 8,502,148 B2* | 8/2013 | Wagner et al. | 250/338.1 |
| 8,709,817 B2* | 4/2014 | Durack et al. | 436/63 |
| 8,727,131 B2* | 5/2014 | Desphande et al. | 209/552 |
| 8,765,062 B2* | 7/2014 | Linder et al. | 422/82.05 |
| 2003/0000835 A1* | 1/2003 | Witt et al. | 204/451 |
| 2005/0178700 A1* | 8/2005 | Tyvoll et al. | 209/631 |
| 2009/0108190 A1* | 4/2009 | Plewa et al. | 250/251 |
| 2012/0277902 A1* | 11/2012 | Sharpe et al. | 700/223 |
| 2013/0242301 A1 | 9/2013 | Berg et al. | |
| 2014/0091014 A1* | 4/2014 | Wagner et al. | 209/579 |
| 2014/0170697 A1* | 6/2014 | Sharpe et al. | 435/30 |
| 2014/0248656 A1* | 9/2014 | Demirci et al. | 435/30 |

OTHER PUBLICATIONS

Asher, S. A., R. W. Bormett, X. G. Chen, D. H. Lemmon, N. Cho, P. Peterson, M. Arrigoni, L. Spinelli, and J. Cannon, "UV resonance Raman spectroscopy using a new cw laser source: convenience and experimental simplicity," Applied Spectroscopy 47, 628-633 (1993).
Ashkin, A., "Acceleration and trapping of particles by radiation pressure," Phys. Rev. Lett. 24, 156-159 (1970).
Ashkin A., and J. M. Dziedzic, "Optical trapping and manipulation of viruses and bacteria," Science 235, 1517-1520 (1987).
Bauer, A., J. Ray, and D. M. Sonnenfroh, "Spark-induced breakdown spectroscopy-based classification of bioaerosols," IEEE International Workshop on Safety, Security & Rescue Robotics (SSRR). (2009). DOI: 10.1109/SSRR.2009.5424145.
Finke, J. R., C. L Jeffrey and R. E. Spjut, "Measurement of the emissivity of small particles at elevated temperatures," Opt. Eng. 27, 684-690 (1988).
Gucker, F. T., C. T. O'Konski, H. B. Pickard, and J. N. Pitts, Jr., "A photoelectronic counter for colloidal particles," J. Am. Chem. Soc. 69, 2422-2431 (1947).
Guicheteau J., S. Christesen, D. Emge, A. Tripathi, "Bacterial mixture identification using Raman and surface-enhanced Raman chemical imaging," J. Raman Spectroscopy. 41, 1632-1637 (2010).
Holler, S., Y.-L. Pan, R. K. Chang, J. R. Bottiger, S. C. Hill, and D. B. Hillis, "Two-dimensional angular optical scattering for the characterization of airborne microparticles," Opt. Lett. 23, 1489-1491 (1998).
Hug, W. F., R. D. Reid, R. Bhatia, and A. L. Lane, "A new miniature, hand-held, solar-blind, reagentless standoff chemical, biological and explosives (CBE) sensor," Chemical, Biological, Radiological, Nuclear, and Explosives (CBRNE) Sensing IX, Eds., A. W. Fountain III, P. J. Gardner, Proc. of SPIE vol. 6954, 695401, 1-9 (2008).
Hybl, J. D., S. M. Tysk, S. R. Berry, and M. P. Jordan, "Laser-induced fluorescence-cued, laser-induced breakdown spectroscopy biological-agent detection," Appl. Opt. 45, 8806-8814 (2006).
Kaye, P. H., J. E. Barton, E. Hirst, and J. M. Clark, "Simultaneous light scattering and intrinsic fluorescence measurement for the classification of airborne particles," Appl. Opt. 39, 3738-3745 (2000).

Kaye, P. H., W. R. Stanley, E. Hirst, E. V. Foot, K. L. Baxter, and S. J. Barrington, "Single particle multichannel bio-aerosol fluorescence sensor," Opt. Express 13, 3583-5393 (2005).
Kaye, P. H., E. Hirst, R. S. Greenaway, Z. Ulanowski, E. Hesse, P. J. DeMott, C. Saunders, and P. Connolly, "Classifying atmospheric ice crystals by spatial light scattering," Opt. Lett. 33, 1545-1547 (2008).
King, M. D., K. C. Thompson, and A. D. Ward, "Laser tweezers Raman study of optically trapped aerosol droplets of seawater and oleic acid reacting with ozone: implications for cloud-droplet properties," J. Am. Chem. Soc. 126, 16710-16711 (2004).
Kong, L. B., P. F. Zhang, G. W. Wang, P. Setlow, and Y. Q. Li, "Characterization of Bacterial Spore Germination Using Integrated Phase Contrast Microscopy, Raman Spectroscopy, and Optical Tweezers," Analytical Chemistry, vol. 82, No. 9, 3840-3847. (2010).
Lewittes, M., S. Arnold, and G. Oster, "Radiometric levitation of micron sized spheres," Appl. Phys. Lett. 40, 455-457 (1982).
Pan, Y.-L., J. !darlings, R. G. Pinnick, S. C. Hill, J. Halverson, and R. K. Chang, "Single-particle fluorescence spectrometer for ambient aerosols," Aerosol Science and Technology 37, 628-639 (2003).
Pan, Y.-L., R. G. Pinnick, S. C. Hill, and R. K. Chang, "Particle-fluorescence spectrometer for real-time single-particle measurements of atmospheric organic carbon and biological aerosol," Environ. Sci. Technol. 43, 429-434 (2009).
Pinnick, R. G., S. C. Hill, Y.-L. Pan, and R. K. Chang, "Fluorescence spectra of atmospheric aerosol at Adelphi, Maryland, USA: measurement and classification of single particles containing organic carbon," Atmospheric Environment 38, 1657-1672 (2004).
Preston, R. E., T. R. Lettieri, and H. G. Semerjian, "Characterization of single levitated droplets by Raman spectroscopy," Langmuir 1, 365-367 (1985).
Shvedov, V. G., A. S. Desyatnikov, A. V. Rode, W. Krolikowski, and Y. S. Kivshar, "Optical guiding of absorbing nanoclusters in air," Opt. Express 17, 5743-5757 (2009).
Shvedov, V. G., C. Hnatovsky, A. V. Rode, and W. Krolikowski, "Robust trapping and manipulation of airborne particles with a bottle beam," Opt. Express 19, 17350-17356 (2011).
Thurn, R., and W. Kiefer, "Structural resonances observed in the Raman spectra of optically levitated liquid droplets," Appl. Opt., 24, 1515-1519 (1985).
Tripathi, A., R. E. Jabbour, J. A. Guicheteau, S. D. Christesen, D. K. Emge, A. W. Fountain, J. R. Bottiger, E. D. Emmons, and A. P. Snyder, "Bioaerosol analysis with Raman chemical imaging microspectroscopy," Anal. Chem. 81, 6981-6990 (2009).
Vehring, R., C. L. Aardahl, G. Schweiger and E. J. Davis, "The characterization of fine particles originating from an uncharged aerosol: size dependence and detection limits for Raman analysis," J. Aerosol Sci. 29, 1045-1061 (1998).
Zhang, P, Z. Zhang, J. Prakesh, S. Huang, D. Hernandez, M. Salazar, D. N. Christodoulides and Z. Chen, "Trapping and transporting aerosols with a single optical bottle beam generated by moire techniques," Opt. Lett. 36, 1491-1493 (2011).
Arthur Ashkin, "Optical trapping and manipulation of neutral particles using lasers," Proc. Natl. Acad. Sci. USA, vol. 94, pp. 4853-4860, May 1997.
David G. Grier, "A revolution in optical manipulation," Nature, vol. 424, pp. 810-816, Aug. 14, 2003.
Pengfei Zhang, et al., "Multiple-trap laser tweezers Raman spectroscopy for simultaneous monitoring of the biological dynamics of multiple individual cells," Optics Letters, vol. 35, No. 20, pp. 3321-3323, Oct. 15, 2010.

* cited by examiner

Figure 1 (BACKGROUND)

SYSTEMS AND METHODS FOR INDIVIDUALLY TRAPPING PARTICLES FROM AIR AND MEASURING THE OPTICAL SPECTRA OR OTHER PROPERTIES OF INDIVIDUAL TRAPPED PARTICLES

CROSS REFERENCE TO RELATED APPLICATION(S)

The present application claims the benefit of U.S. Provisional Patent Application No. 61/665,031 filed Jun. 27, 2012, herein incorporated by reference in its entirety herein.

GOVERNMENT INTEREST

The invention described herein may be manufactured, used and licensed by or for the U.S. Government without the payment of royalties thereon.

It resulted from research supported by the U.S. Army Research Laboratory (ARL) Director's Research Initiative (DRI) project (FY 2010-2011 CIS-05).

BACKGROUND OF THE INVENTION

1. Field

Embodiments of the present invention are generally directed to measuring optical spectra of other properties of airborne particles that can be used for detection or characterization of particles in air, including harmful biological and chemical particles in air.

2. Description of Related Art

Airborne particles pose many problems. They can impact human health, agriculture, and the earth's climate. Pollens and fungal spores can cause allergies such as hay fever. Asthma can be exacerbated by airborne particles such as pollens and pollen fragments, particles from fungi, including fungal spores, bacteria, proteins from cats and dogs, and particles from cockroaches, and dust mites. Airborne particles, primarily bacteria and viruses, but also some fungi, are a primary means of disease transmission in humans and other animals. Fungal spores and bacteria transmit diseases of agricultural crops that are responsible for tremendous losses each year.

Primary Biological Aerosol Particles (PBAP) include bacteria, fungi, pollens, viruses, algae, protein allergens from cats and other animals, bits of leaves, plants, skin, dandruff, etc. These particles may be aerosolized by airflows, abrasion, and by injection (e.g., sneezing by animals or expulsion of spores by fungi). In addition to these commonly-identified particles, the PBAP may also include fragments of those particles, e.g., micron-sized particles that form when pollen grains undergo osmotic shock and rupture within the anthers or catkins of anemophilous plants may later be released into the air to form a respirable, antigen laden aerosol. Similarly, allergen-laden fungal fragments can be much smaller than the fungal spores. PBAP also includes re-aerosolized materials. Plants, fungi, and some animals have evolved efficient mechanisms to inject their pollens, spores, or their offspring, etc., into the air.

There are large differences in the estimates of both PBAP emissions into the atmosphere and atmospheric loadings. PBAP has been reported to contribute as much as 25% of the total mass of atmospheric particulate matter. Fluorescent biological aerosol particles were found to contribute 28% of the total particle number (in the 0.8-20-mm diameter range) above a forest canopy in Borneo, Indonesia. The global average concentration of fungal spores has been estimated to be approximately 1 mg/m$^3$. There are large differences in estimates of total PBAP emissions.

FIG. 1 is a schematic illustration of some sources of atmospheric aerosols and their chemical and photochemical transformations. An atmospheric aerosol 10 can be extremely complex. Biological particles found in the atmosphere may include organisms such as bacteria, fungal spores, viruses, pollens, fragments of plants, fungi, etc. Complex mixtures can occur in particles because of (a) emission of complex particles, (b) adsorption of gasses by particles, (c) agglomeration of particles, (d) chemical and photochemical reactions of particles, and (e) cycling of particles through clouds. Sunlight provides the energy necessary for many chemical reactions in particles. Long range transport occurs over thousands of miles, such as for example, from China to California and from the Sahara Desert to the Carolinas.

Many particles in the atmosphere are complex mixtures. These result from emissions of complex particles, and adsorption, agglomeration, chemical reactions which can occur, especially in cycling though clouds. Sunlight provides the energy for many atmospheric chemical reactions affecting particle composition. Bacteria, pollens and other PBAP can also act as cloud condensation nuclei, and thereby affect rain deposition patterns, cloud coverage, and global climate. Also, many PBAP, including many pollen and fungal particles, and other carbon-containing aerosols (e.g., soot) absorb atmospheric radiation and re-emit some of that radiation at ultraviolet and visible wavelengths. Therefore, the absorption and fluorescence properties of atmospheric pollen and fungal materials are relevant for understanding their effects on climate. Some of the, if not the, largest uncertainties in global climate models are attributable to the uncertainties regarding the effects of aerosols. Some aerosols (e.g., soot) can contribute to warming by absorbing light. Other aerosols (composed of, e.g., bacteria, silica dust, or ammonium sulfate) can contribute to cooling by scattering light or by acting as cloud condensation nuclei which help generate cloud droplets which also scatter light, preventing sunlight from reaching the earth.

Optical trapping and manipulation of micron-sized particles, nanoparticles, molecules, and atoms have been used in aerosol science, chemistry, physics, biology, and interdisciplinary studies. For example, in one type of radiation pressure trap, commonly referred to as optical tweezers, a tightly-focused beam is used to hold particles. Other optical trapping methods have also been reported, e.g., using longitudinal trapping, holographic methods, self-reconstructing beams, and axicon(s). Combinations of trapping with other analytical techniques, e.g., Raman spectroscopy of particles in air or in liquid, provide ways to analyze molecular composition and to study time-varying phenomena, e.g., dynamic reactions in individual living cells.

Methods and devices exist for counting and characterizing airborne pollens, fungal and plant spores, bacteria, protein allergens, and other PBAP.

These techniques, however, are not without drawbacks. For example, airborne biological agents, such as anthrax or plague, can be dispersed at such low concentrations that no one would suspect a release until after persons got sick and went to the doctor. Although, forecasts related to allergens are available in much of the world, counting and classifying pollens to the genus or species level is presently performed by labor-intensive microscopic analysis of collected samples. At present, it is prohibitively expensive to measure bacteria, protein toxins or allergens, pollen and fungal spores with sufficient spatial and temporal resolution and specificity to provide adequate warning of a bioagent attack, or to provide adequate forecasts for persons with allergies. The times required for sampling and analyzing airborne bacteria, pollen and fungal particles preclude real-time alerts of hazardous conditions, and they make more difficult potential studies of the effects of bacteria, pollens or fungal particles on atmospheric processes, or studies of transmission of fungal diseases of plants.

Improved, automated, and near-real-time techniques for characterizing bacteria, pollens, fungal spores, and other PBAP may be useful.

BRIEF SUMMARY OF THE INVENTION

Embodiments of the present invention are directed to systems and methods for sampling atmospheric particles by trapping particles from air and measuring the optical spectra and/or other properties of (typically) individual trapped particles.

According to one embodiment, a system for continuously sampling particles from air may include: an airflow system configured to continuously draw air including airborne particles into the system; a photophoretic trap that uses photophoretic forces of a laser beam to trap one or more of the airborne particles from the drawn air; a measurement device configured to measure one or more properties of the trapped one or more airborne particles; and a controller configured to repeatedly trap, measure and release one or more airborne particles.

According to another embodiment, a method for continuously sampling particles from air may include: continuously directing air including airborne particles toward a photophoretic trap that uses photophoretic forces of a laser beam to trap one or more of the airborne particles; detecting an airborne particle in the air approaching and/or within the photophoretic trap; trapping one or more airborne particles in the photophoretic trap; measuring one or more properties of the trapped one or more airborne particles; and releasing the trapped one or more airborne particles.

These and other embodiments of the invention are described in more detail, below.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments, including less effective but also less expensive embodiments which for some applications may be preferred when funds are limited. These embodiments are intended to be included within the following description and protected by the accompanying claims.

FIG. 15A shows the Raman scattering signal of a particle measured using data acquisition conditions extending over a 30 second interval, slit width 500 μm; and Gain=2 for the EMCCD.

FIG. 15B shows the Raman scattering signal of a particle measured using data acquisition conditions extending over a 30 second interval; slit width 100 μm; and Gain=5 for the EMCCD.

FIG. 15C shows the Raman scattering signal of a particle measured using data acquisition conditions extending over a ½ second time interval; slit width 500 μm; and Gain=100 for the EMCCD.

DETAILED DESCRIPTION OF THE INVENTION

Figure 1:
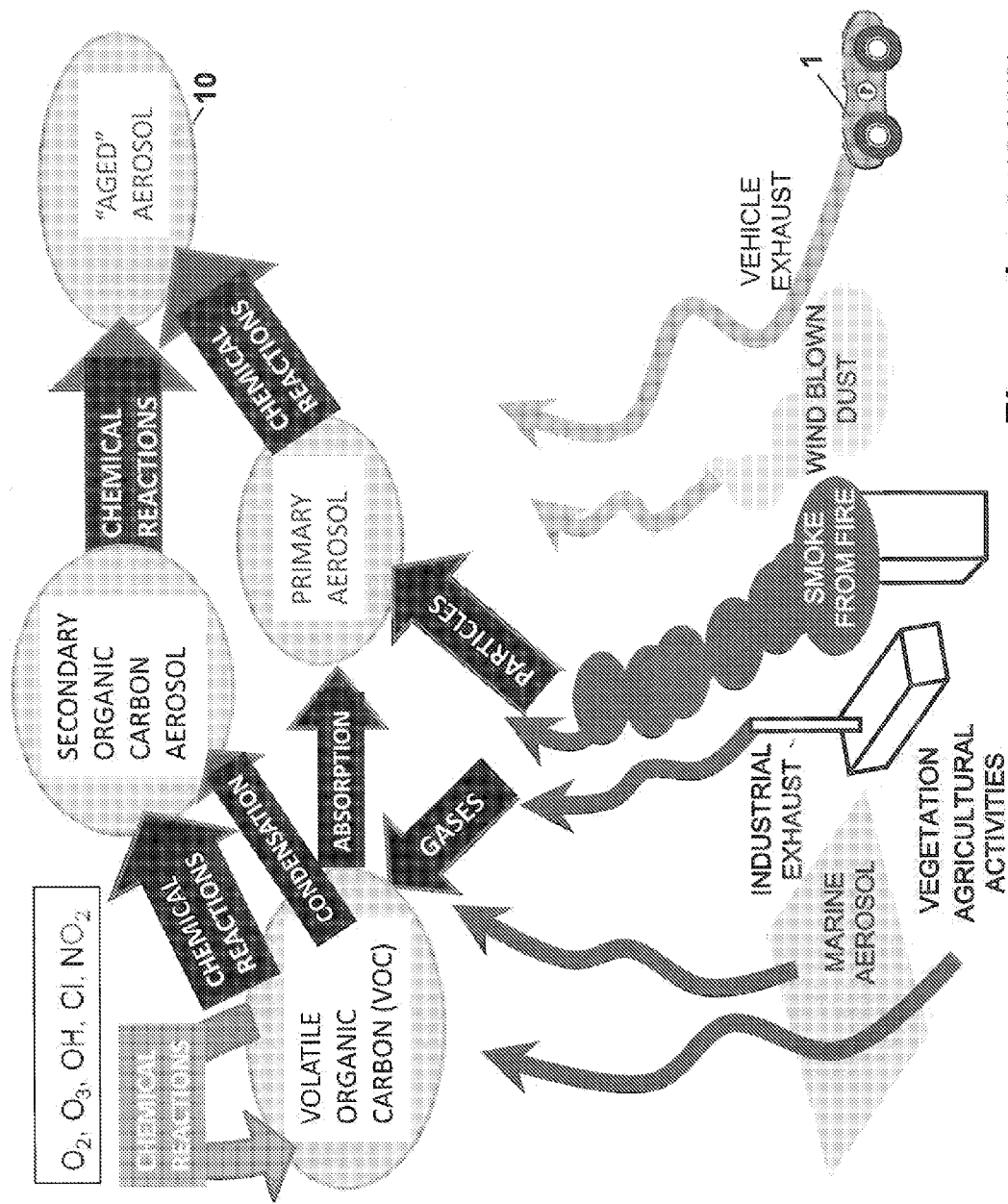
FIG. 1 is a schematic illustration of some sources of atmospheric aerosols and their chemical and photochemical transformations.

Embodiments of the present invention are directed to systems and methods for continuously sampling particles from air. These embodiments enable individually trapping particles from air and one or more measurements of individual trapped particles. Measurements may include the optical spectra and/or other properties of the trapped particle.

By using a photophoretic trap which traps and holds a particle in a sampling volume, one or more measurements of trapped airborne particles may be made "one-particle-at-a-time," i.e., in an individual or substantially individual manner, because the trap inhibits other particles that might become trapped from entering the trap. When a particle approaching and/or within the trapping volume is detected, the photophoretic trap may be actuated so as to trap the particle for measurement. Alternatively, if a particle is already held in the photophoretic trap, once detected, it can be measured. Additional measurements of the same trapped particle may be made, if desired. After measurements, the trapped particle may be released, and depending upon the measurements of the particle, may be collected for further analysis.

Measurements on a single trapped particle that is held in a very small spatial region, i.e., within the trapping volume, can be more precise and have a better signal-to-noise ratio than measurements made on particles flowing or held within a larger volume in air and/or measurements made of multiple particles at once. For example, in looking for a minor particle species mixed with a much larger group of other types of particles (a typical situation in atmospheric sampling) embodiments of the present invention will be far more sensitive than techniques that examine many particles (e.g., 100's to 1000's) simultaneously. Embodiments of the present invention reduce the number of false positive indications of specific harmful particles in the air (as compared to conventional "trigger" instruments).

The measurements may include measuring one or more optical (e.g., Raman, fluorescence, infrared emission) spectra and/or other properties of the trapped particle, for instance. The measurements can be used for detection of harmful biological and chemical particles in air, including biowarfare agents, or can be used otherwise for characterization of particles in air. This system may be beneficial for measuring airborne particles which may only be present in a very small concentration relative to concentrations of other particles in air (e.g., less than one particle in 10, one particle in 100, or one particle in 1000). Where multiple measurements are performed, the combination of data obtained from the multiple measurements of a single particle can nonetheless be extremely powerful.

Accordingly, embodiments of the present invention may provide substantially "real-time" (e.g., within a few seconds) monitoring of airborne particles. Also, they may run continuously without using any reagents or liquids, or special surfaces on which to catch the particles, and thereby, the logistics for operating the system are minimized. That is, the costs in operator time to service the instrument, replenish reagents, filters, collection surfaces, etc., and the costs in storage and transportation of reagents, etc., are minimized.

Figure 2:
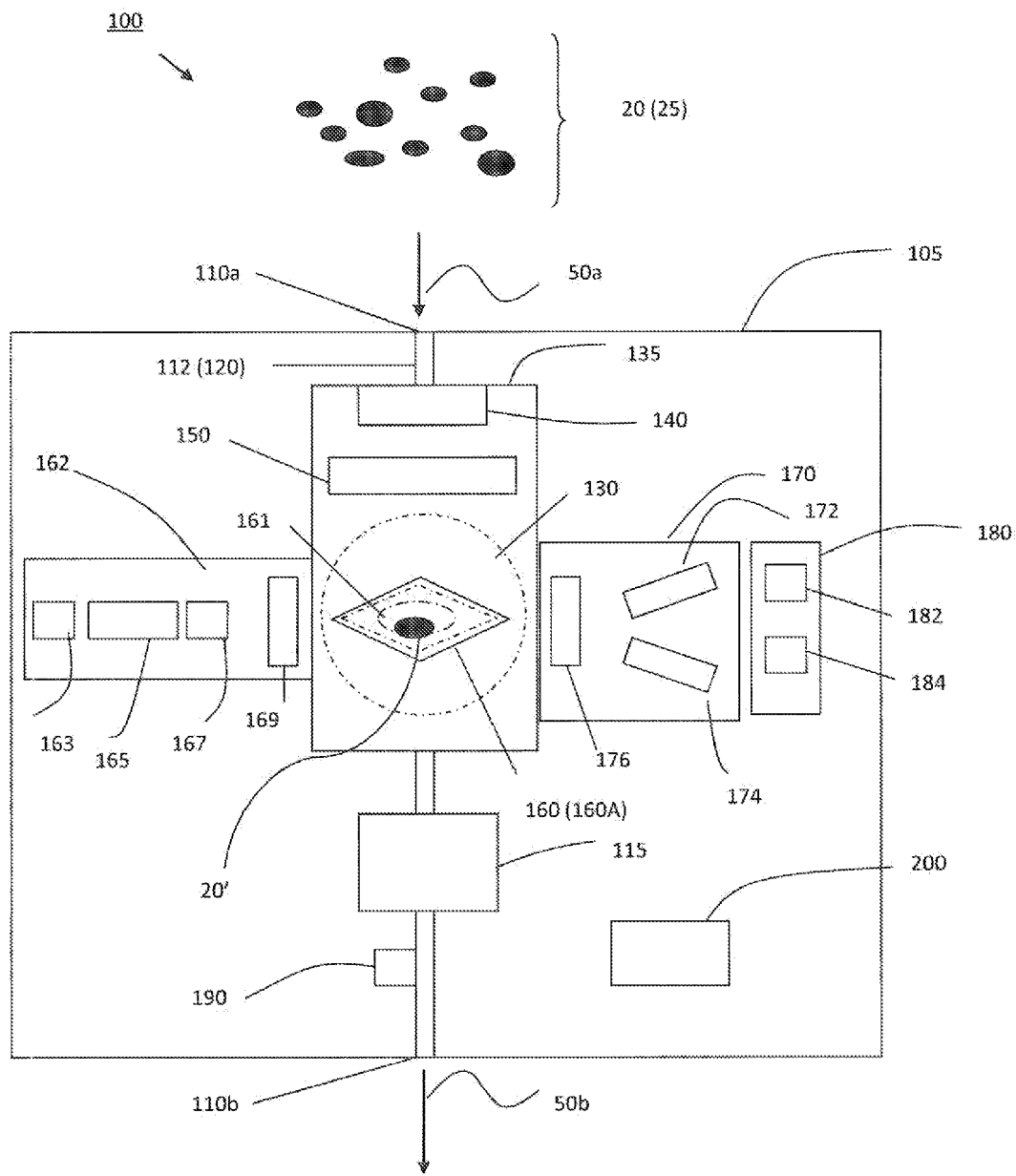
FIG. 2 shows a schematic illustration of a system for continuously sampling particles from air according to an embodiment of the present invention.

FIG. 2 shows a schematic illustration of a system for continuously sampling particles from air according to an embodiment of the present invention.

Various elements of the system 100 may be incorporated into a housing or other structure 105, thus forming a unitary apparatus. The housing 105 may also include an appropriate power supply, for instance. As such, the system, embodied as an apparatus, may provide a compact and portable device. In some embodiments, not all elements illustrated in the figure will be provided, and/or other elements may be provided. Additionally, it will be appreciated that the elements may be present or may be positioned in locations other than illustrated in this schematic.

The system 100 includes an airflow system 120 configured to draw one or more airborne particles 20 into a trapping volume 160A (i.e., the volume depicted in dotted line enclosed and defined by the photophoretic trap 160 depicted in solid line, further discussed below). Particles within this trapping volume 160A can be trapped and held for measuring, typically, in a smaller central measuring volume 161 within the trapping volume 160A, as explained later.

As shown, there is a measuring volume 161 depicted as a smaller volume within the trapping volume 160A defined by the photophoretic trap 160. The trap 160 is located within a sampling volume 130 of the system 100. For instance, in one embodiment, the sampling volume 130 and the trapping volume 160A may be substantially the same size and overlap in a location within the system. In other embodiments, the trapping volume could be made relatively large and the sample volume could be made small, and the air could be directed toward the trap. That arrangement may increase the fraction of particles, drawn into the device, that are caught in the trap, which can be beneficial for situations where the particles have been pre-selected in some way, or are expensive or hard to obtain. Other measurements of properties (such as temperature, humidity, density) of the air drawn into the box 135, or of airborne particles 20 drawn into the box 135, or of the flow rate of the air drawn into the box 135 may be measured. Additional measurement(s) of particles 20, not requiring trapping individual particles 20', may also be measured in the sampling volume 130. Other configurations of the sampling volume 130 are also possible.

Particles 20 may be suspended in a gaseous medium 25 air, typically atmospheric air, or some other gas. In various implementations and uses, the particles may include, e.g., solid, liquid, gel, and/or mixtures of these dispersed in a gas, which may be consistent with the usual and customary definitions of aerosol particles. The system may be configured so that all the particles drawn into the system pass through the trapping volume 160A, or it may be configured so that only a fraction of the particles are drawn through the trapping volume 160A. While a particle 20 is held in the trapping volume 160A of the photophoretic trap 160, airflow may continue substantially unabated through the trap 160, around the trap 160, or some combination thereof.

The size of the particles 20 may vary depending on the environment and/or desired application(s). Airborne particles 20 ranging from 0.6 to 100 micrometers may be quite common in some environments. Typical sizes of bacteria and bacterial spores may range from 0.6 to 10 μm. Typical sizes of anthrax spores range from 1.1 to 1.7 μm in length and 0.8 to 0.9 μm in diameter. Typical sizes of fungal spores may range 2 to 20 μm in diameter. Corn pollen typically can be 80 to 100 μm in diameter.

The airflow system 120 creates a flow of air 50. The incoming airflow 50a (to the system 100) flows into an inlet 110a and then to the sampling volume 130. The outgoing airflow 50b (from the system 100) flows via an outlet 110b to the ambient environment. A filter and/or grating (not shown) may be provided at the inlet 110a, if desired, to prevent particles larger than a predetermined size from entering the system. Tubing 112 may provide fluid connection for airflow 50 through the system 100. Here, reference numeral 112 points specifically to an inlet tube of tubing 112. A fluid mover 115 may be provided which creates sufficient force (e.g., negative pressure) to move the airflow 50 into and through the system 100. For example, the fluid mover 115 may be a pump, a fan, a compressor, a blower, a corona-generated ion wind, etc. To avoid violent or turbulent flow, the fluid mover 115 may be operated to ensure the flow rate of airflow 50 is laminar with a steady flow rate. To avoid large drag forces on particles, which may require very strong photophoretic forces to be held, the airflow rates will typically be less than 1 m/s, and may be less than 1 cm/s. Lower airflow and particle velocities allow particles to be trapped with lower requirements for trapping laser power, for a given trap design. However, when the airflow rates are decreased, in order to reduce the requirements for trapping (such as, the trapping laser intensity), the sampling rate tends to decrease. The drag force on a spherical particle of diameter d in a gas flow of velocity V and viscosity η is $F_D = 3\pi\eta Vd$. While the fluid mover 115 is illustrated near the outlet 110b of the system 100, as it is a preferred embodiment because the particles do not need to pass through any fluid mover before they are measured. But it will be appreciated that the fluid mover 115 can be located at another location in the airflow 50, such as, for example, near inlet 110a.

The sampling volume 130 may be located within a substantially airtight box 135 having an inlet and an outlet. Inside the box 135, air and particles pass through an optional particle concentrator 140 which increases the concentration or density of the particles in the airflow 50. The particle concentrator 140 may be a so-called "air-to-air" concentrator, for instance, for specifically processing particles in a gaseous medium.

A particle detector 150 is configured to detect a particle (or particles) approaching and/or within the sample volume 130. In one embodiment, the particle detector 150 may include one or more trigger beams. When a particle scatters light from the beam or beams, and this light is detected by one or more photodetectors, the signals from the photodetector or photodetectors indicate the presence of a particle either approaching and/or within the trapping volume 160A, depending upon the precise alignment of the trigger. As shown, the particle detector 150 is positioned somewhere upstream of the trapping volume 160A. But, in other embodiments, trigger beams of the particle detector 150 could overlap with the sampling volume 130 and/or the trapping volume 160A. For example, the particle detector 150 may be comprised of two different-wavelength crossed-beam diode lasers with corresponding photodetectors, each of said photodetectors including an optical filter that passes the wavelength of the diode laser it detects and blocks the light from the other diode laser and light at any other wavelengths that would interfere. One crossed diode trigger laser system which may be used as a particle detector 150 is described, for example, in U.S. Pat. No. 6,947,134, herein incorporated by reference. Of course, other trigger beam systems and devices might also be used for detection a particle. For detection of a particle within (not approaching) the trapping volume, the particle detector 150 could at least partially overlap the trapping volume 160A in the schematic drawing.

In other embodiments, the photophoretic trap generator system 162 (discussed in more detail below) can be used to provide a beam for detecting a particle approaching and/or within the trapping volume 160A, thus forming the particle detector 150. Here, the photophoretic trap generator system 162 may operate as follows: 1) the trapping laser 165 is gated off (or turned "off", or modulated to a relatively low intensity) for a short time (e.g., 1 ms) to let any trapped particle (typically as soon as the measurement of the trapped particle is completed) out of the trapping volume 161, and to let new particles into the trapping volume 161; 2) the trapping laser 165 is gated on (or turned "on", or modulated to be at a higher intensity) to trap any particle that is in the sample volume; 3) a portion of the beam from the trapping laser 165 illuminates the trapping volume 160A and is scattered by particles, if any, trapped in the trapping volume 160A; 4) the scattering is detected, for instance, using a measuring device, such as a photomultiplier (PMT) or photodiode system, configured with the detection threshold set to trap only particles having a diameter greater than some desired size, as in the trigger system described in U.S. Pat. No. 6,947,134; 5) if a particle is detected, the measurements are begun. After completion of the measurement(s), the process may be repeated, and in a typical embodiment is repeated continuously as soon as a particle is trapped and its desired properties have been measured. This approach may provide a less expensive, system by eliminating the separate trigger lasers and their associated photodetectors, filters, lenses and holders for this subsystem. It may also obviate the need for careful alignment of the trigger beams. The photophoretic trap 160 traps a particle 20' in the trapping volume 160A (a volume defined by the photophoretic trap 160) and holds it therein. Photophoretic forces generated by the photophoretic trap 160 will tend to urge the particle 20' toward a central measuring volume 161 of the photophoretic trap 160; thus, the volume in which the particle is held during measurement of it optical properties is typically much smaller than the volume 160A defined by the light beams of the photophoretic trap 160. Ideally, the photophoretic trap 160 is sized and configured to trap and hold one individual particle 20' at a time from the airflow 50. It is noted that this is the expected performance of the photophoretic trap 160.

However, there may be circumstances (e.g., relatively high concentrations of particles 20 in the inlet air) in which more than one particle might be trapped and held. This is a result of the typical substantially random distribution of particles in air. But the probability of trapping and holding two or more particles (e.g. greater than 0.5 micrometer) at once is likely to be very low (e.g., less than 1% of the time) if the average concentration of particles in air is low enough that only one particle is in the trapping volume at any time. For instance, the particle concentration could be diluted by combining the inlet air with clean air, or by enclosing the inlet airflow within a clean air sheath. In any event, the photophoretic trap 160 can be configured to trap and hold about one particle for measurement(s) thereof (i.e., where the vast majority of the measurements are of a single individual particle, and only some small fraction of the measurements are of two or more particles with sizes greater than some minimum diameter, e.g., 0.6 micrometer).

For some applications, embodiments that measure average spectra for multiple particles may be adequate, and in fact desired, for example, because the measurements could be made more quickly. For example, in monitoring the smoke particles from a fire, or the exhaust from an engine, trapping many particles at once, can provide a way to rapidly provide the average spectra of the particles, which may be desirable because, for example, such particles may change rapidly as the engine or fire parameters vary.

The photophoretic trap 160 is formed by photophoretic forces which trap an airborne particle and hold it. Here, the photophoretic forces may be generated by the photophoretic trap generator system 162 which may include a beam controller 163, laser 165, and optical system 167. The beam controller 163 is configured to modulate the intensity of the laser 165. The trapping laser 165 is actuated or unblocked (or gated-on) or modulated to a higher intensity, for example, at an appropriate time to trap a particle.

The photophoretic trap is specifically configured to generate photophoretic forces to trap and hold a particle. Photophoretic forces on a particle in air result when one side of the particle absorbs more electromagnetic energy (light) than the other side, and consequently becomes warmer than the other side. The warmer side heats the air adjacent to it, causing the air molecules to move faster, and to impart more momentum to the particle on the warmer side. Consequently, there is a net force pointing in the direction from the warmer to the cooler side. If a light-absorbing particle is in a region where the light intensity on one side is greater than the intensity on the other side, the particle tends to absorb more light on the side with the greater light intensity. Then, the photophoretic forces push the particle away from the high-intensity region toward a region with lower intensity. If the particle is weakly absorbing of light, the heating pattern in and immediately outside the particle can be more complex. In some instances, particles that are highly absorbing of light at the laser wavelengths used may be of interest.

For some excitation wavelengths, and size, absorptivity, and thermal conductivity of the particle, the temperature difference between the two sides of the particle may, because of thermal diffusion, be smaller than desired for strong photophoretic trapping. Therefore, in some embodiments, a high-repetition-rate pulsed laser is used for trapping. Each pulse generates a large temperature gradient across the particle, which may decrease rapidly with time. The large temperature gradient may then be generated again by the next pulse.

For relatively transparent particles in relatively transparent media, the gradient force (a subset of radiation pressure forces) can be stronger than the photophoretic force. Thus, the particles may be attracted toward to the strongest electric field. On the other hand, for particles that absorb light strongly, the photophoretic force can be orders of magnitude larger than the radiation pressure force. Photophoretic forces thus push particles away from the high-intensity region, and therefore, different light-intensity configurations are required for trapping absorbing particles stably. Non-absorbing particles tend to be caught in the high-intensity beam and be drawn to the regions of highest focus (not at the center of the photophoretic trap), or they are not caught at all.

Various methods may be used to control the amplitude of the laser beam 165 that generates the photophoretic trap. If the trapping laser 165 is a diode laser that can be controlled by varying its drive current, then the beam amplitude (and trap) can be controlled by varying the drive current. And if the laser is one where the amplitude cannot be directly controlled sufficiently rapidly using fast electronics (e.g., in the beam controller 163), then other modulators or shutters could be used. For example, a separate blocking or modulating element 169 may be provided in various embodiments. This blocking or modulating element 169 is configured to be actuated so as to block the laser trapping beam from reaching the trapping volume 160A, or to modulate the laser trapping beam so as to photophoretically move selected particles out of the trapping volume 160A, or photophoretically move the selected particle to one or more collection surfaces, depending upon the results of the measurements and algorithms. The blocking element 169 may include, for instance, an acousto-optic modulator (AOM), electro-optic modulator (EOM), a motor-driven mechanical shutter, or a piezoelectric-driven shutter.

The photophoretic trap 160 may be configured in multiple ways. A variety of methods have been used to generate low optical intensity surrounded on all sides by higher intensity. Such an optical distribution is termed a bottle beam or dark focus region. Some methods that can be used to generate these bottle beams or dark focus regions for trapping and manipulating single or multiple absorbing particles in air employ either a single beam or counter-propagating beams, one lens or multiple lenses or no lens (a circular aperture), or a hologram, or moiré patterns, or axicons in combination with lenses.

Figure 3A:
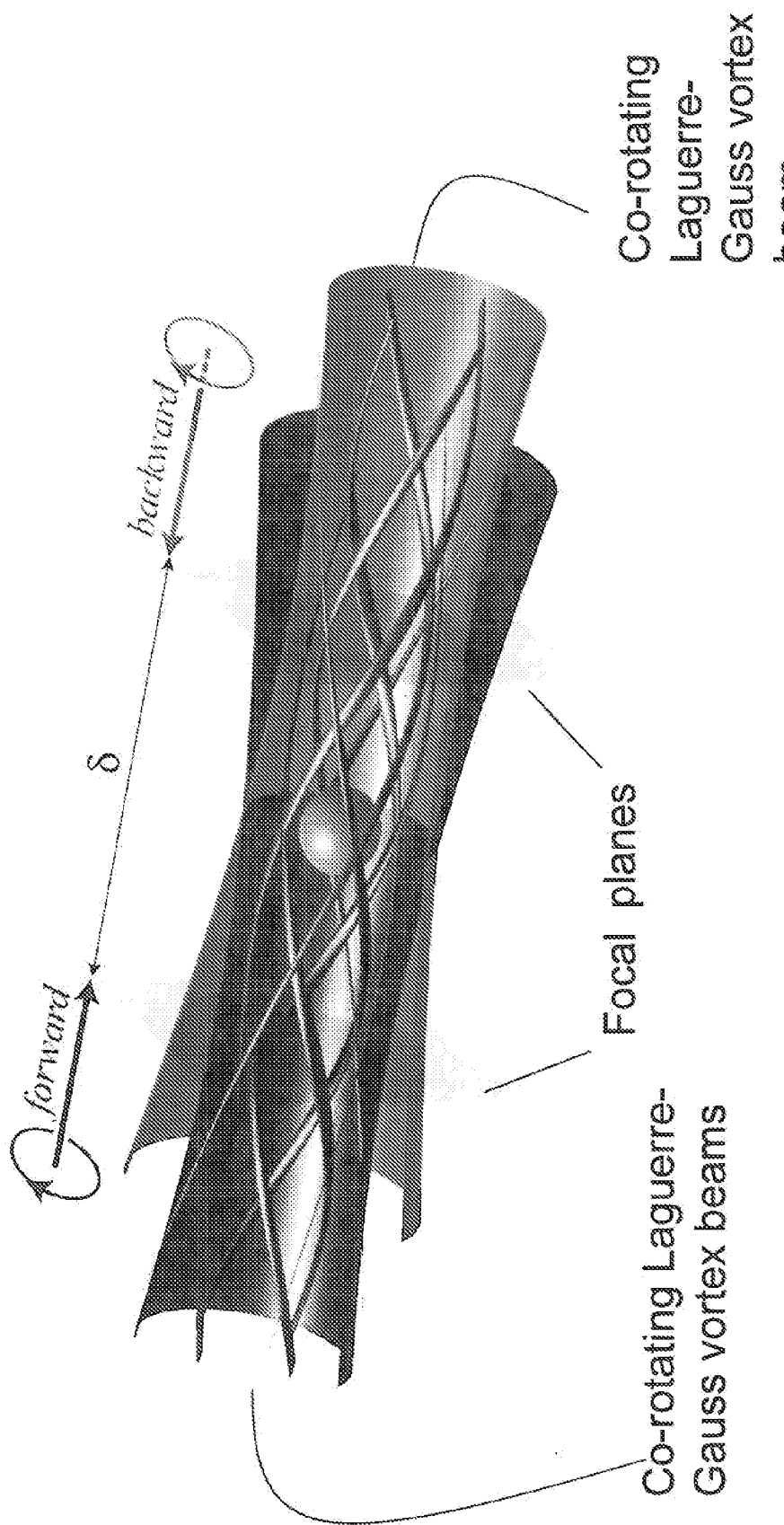
FIG. 3A illustrates a schematic of a photophoretic trap which may be used in embodiments of the present invention.

FIG. 3A shows a schematic of one photophoretic trap having two counter-propagating and co-rotating Laguerre-Gauss vortex beams shown by surfaces at their tube-like intensity maxima which may be used in embodiments of the present invention. Trapping of particles in air using photophoretic forces in this configuration was reported by V. G. Shvedov et al, "Optical guiding of absorbing nanoclusters in air," Opt. Express 17, 5743-5757 (2009), herein incorporated by reference. In Shvedov, et al, (2009) two vortex beams, with their beam waists shifted relative to each other along the axis of the beams, generate a region of low intensity near the axis and away from the two beam waists that is surrounded in any direction by a high-intensity surface of light. The focal (gray) planes of the forward and backward beams are separated by a distance δ. For equal powers of the two beams the trapping position is near the middle, between the plane. A particle is subject to illumination from both sides. Whenever a trapped particle moves in any direction away from the low-intensity region near the center of the trap, it eventually encounters the high intensity light, and photophoretic forces push the particle back toward the center of the trapping volume 160A. The particle eventually reaches a stable position by balancing all the forces.

Figure 3B:
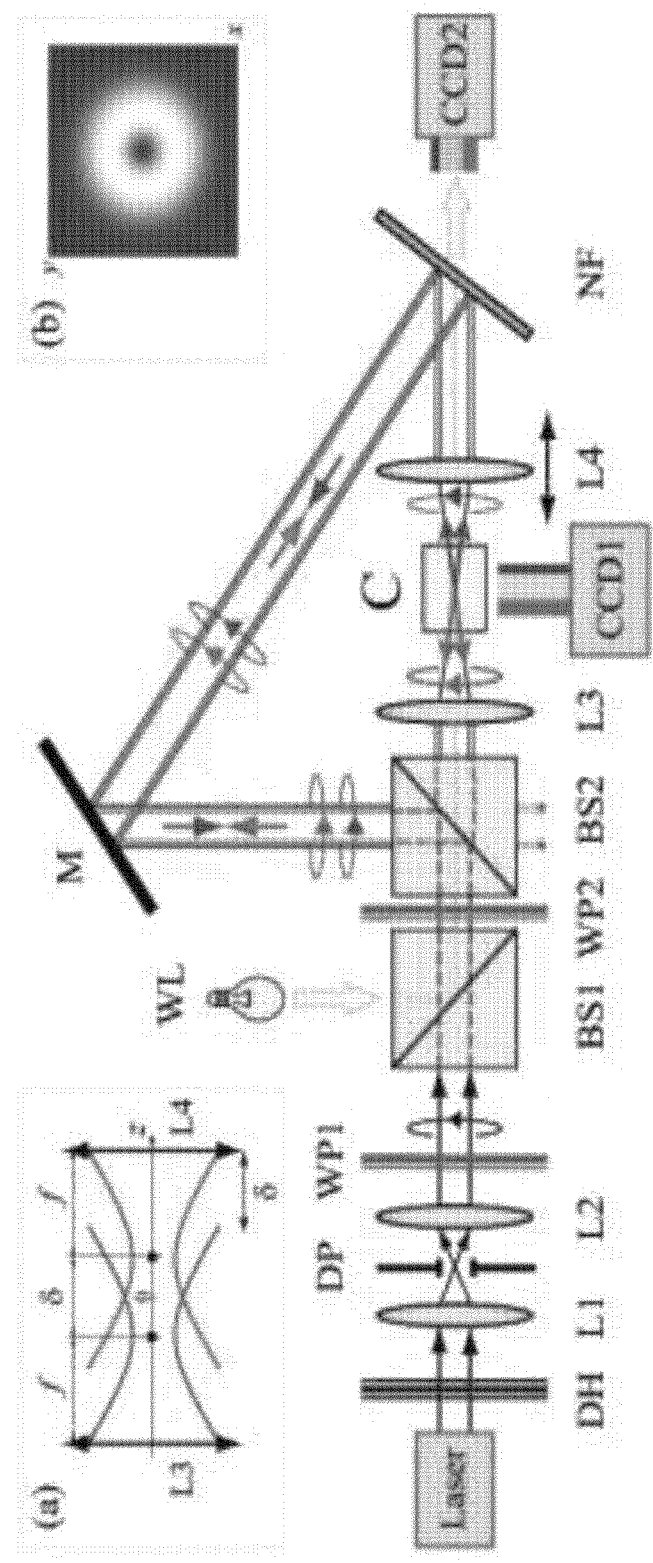
FIG. 3B is an illustration of an experimental photophoretic trap which may be used in embodiments of the present invention.

FIG. 3B is an illustration of the experimental photophoretic trap shown in Shvedov et al. (2009). Inset (a) shows a dual beam vortex trap with movable lens L4 adjusting the separation of focal planes δ. Inset (b) shows the ring-like transverse intensity distribution of a Laguerre-Gauss vortex beam. The trap includes elements: DH—diffraction hologram, L—lenses, DP—diaphragm, WP—half-wave plates, BS—polarizing beam-splitters, WL—white light source, M—mirror, C—trapping region, NF—notch filter. As shown in FIG. 3B, the linearly polarized Gaussian beam derived from a cw laser source (e.g., Verdi V5, Coherent Inc., wavelength λ=532 nm) passes through diffraction fork-type hologram DH (See, He, N. R. Heckenberg, and H. Rubinsztein-Dunlop, "Optical particle trapping with higher-order doughnut beams produced using high efficiency computer generated holograms," J. Mod. Opt. 42, 217 (1995) and I. V. Basisty, M. S. Soskin, and M. V. Vasnetsov, "Optics of light beams with screw dislocations," Opt. Commun. 103, 422-428 (1993)) where it is transformed into a Laguerre-Gauss vortex beam with the topological charge 1=1; the transverse intensity pattern of the beam is shown in the inset (b) of FIG. 3B. The beam diameter can be varied by a collimator based on two lenses, L1 and L2. The half-wave plate WP1 adjusts the polarization of the input vortex beam so that it passes through the polarizing beam splitter BS1. The beam splitter serves as an injector of white light from the source WL to monitor the transverse dynamics of particles trapped in the trapping area C. The white light provides the background illumination for the images of the particles at the CCD2 camera after passing the notch filter NF which cuts off the laser radiation. The interferometer consists of three reflectors—a notch filter NF reflecting the laser beam, a mirror M, and a polarizing beam splitter cube BS2. The beam splitter BS2 divides the vortex beam into the forward-propagating beam (arrows) and the backward-propagating beam (red arrows). The forward beam passes through the lenses L3 and L4, reflects from the notch filter NF and mirror M, and exits the ring trough BS2. The backward beam reflects from BS2 and the mirrors M and NF, enters the trapping area in the opposite direction and goes through L4, L3, to exit the interferometer reflecting from BS2. The scheme is designed so that both beams have only a single round trip, thus preventing unwanted interference of the beams on the following paths. The interferometer is formed with the odd number of reflectors so that the axial symmetry of the intensity distribution is preserved for any polarization state of counter-propagating beams. The particle trapping volume C is formed between the lenses L3 and L4 and the distance 6 between their focal planes can be varied by moving lens L4, see the inset (a) in FIG. 3B. The imaging camera CCD1 collects the light scattered by the particles and monitors the behavior of the trapped particles in the longitudinal direction.

Figure 4:
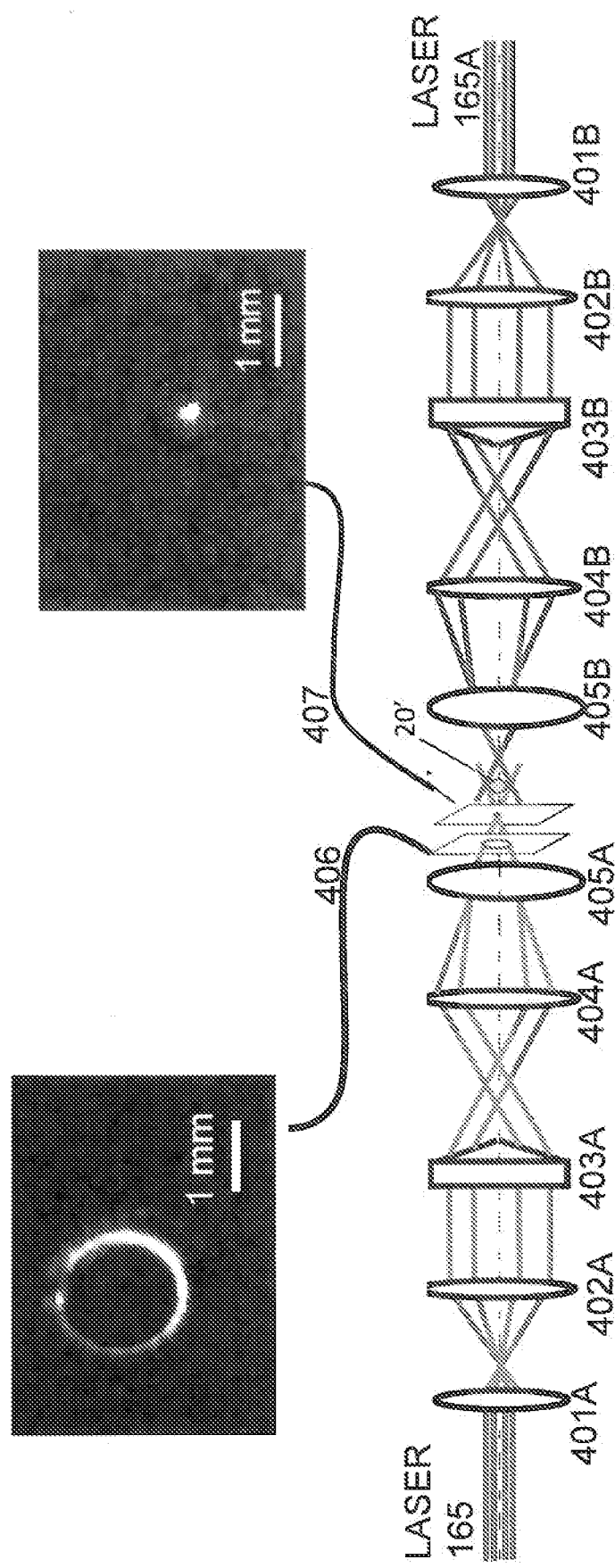
FIG. 4 shows a schematic of a photophoretic trap which may be used in embodiments of the present invention.

FIG. 4 shows a schematic of another photophoretic trap which generates two counter-propagating hollow beams to trap aerosol particles which may be used according to embodiments of the present invention. As used herein, "hollow" does not mean that there is no light intensity along the axis of the cone, but rather that the intensity near the axis near the center of the trap is much lower than near the walls of the cone. Illustrated in FIG. 4 are lasers 165A, 165B at opposing ends pointed in opposing directions. Light from the laser 165A, 165B enters beam expanders 401A, 402A and 401B, 402B, respectively. Light from the beam expanders enters axicon lenses 403A, 403B and is focused by focusing lenses 404A, 404B onto tube lenses 405A, 405B then onto spatial filters 406, 407.

Axicons and other optical components may be used to form two counter-propagating circular hollow laser beams from one laser beam, e.g., from a Gaussian beam from an argon (Ar)-ion-laser beam. As used herein, an "axicon" is an optical element that images a point into a line segment along the optical axis.

The two beams 165, 165A in FIG. 4 may be focused to form hollow conical beams, which overlap to produce a biconical region of low intensity surrounded in any direction by the high intensity regions of the hollow beams, which is a type of bottle beam. This trap is stable for absorbing particles. In this trap Raman spectra can be readily measured from individual micron-sized clusters of multi-walled carbon nanotubes (MWCNTs) in air. This photophoretic trap uses tube lenses and standard lenses as well as axicon lenses. Insets in the figure show intensity distributions of beam profiles measured for only one laser beam. The right inset shows the distribution near the focal region and the left inset shows the distribution farther from the focal region. This arrangement is believed to be simpler and less expensive to produce than some of the previously disclosed trap embodiments.

Other embodiments are possible. For example, the optical bottle-beam trap for photophoretically holding the particles may be generated using:

(a) a single beam and a circular phase plate that causes a phase difference of π radians, similar to that described by Ozeri et al., "Long spin relaxation times in a single-beam blue-detuned optical trap," Physical Review A, 59, 1750-1753 (1999), herein incorporated by reference;

(b) a hologram similar to that described by Arlt and Padgett, "Generation of a beam with a dark focus surrounded by regions of higher intensity: the optical bottle beam," Optics Letters, 25, 191-194 (2000), herein incorporated by reference; or (c) a single Gaussian beam focused with a single lens similar to that described by Shvedov et al., "Robust trapping and manipulation of airborne particles with a bottle beam," Opt. Exp., 19, 17350-17356 (2011), herein incorporated by reference.

Additionally, in other embodiments, a dark focus (bottle beam) region may be generated using a circular aperture similar to that discussed by Garcia-Sucerquia et al., "Tubular structures in diffracted fields," SPIE Vol. 4829, pp. 10-11, (2003), herein incorporated by reference. In other embodiments, the dark focus may be generated as described by Yelin et al., "Generating an adjustable three-dimensional dark focus," Optics Letters, 29, 661-663 (2004), herein incorporated by reference. Bottle beams or dark beams can be generated using phase masks, or using moiré techniques where a computer-controlled spatial light modulator reflects according to the overlap of two gratings as disclosed by Zhang et al., "Trapping and transporting aerosols with a single optical bottle beam generated by moiré techniques," Optics Letters, 36, 1491 (2011), herein incorporated by reference.

The intersection of the multiple hollow trapping beams forms a closed high-intensity axi-symmetric surface. Particles remain trapped because gravitational, drag, and other forces are not sufficient to exceed the photophoretic trapping forces. Thus, there is no need to impart a charge to particles in order for the particles to be trapped as they must be in using electrostatic or electroquastatic forces.

Returning to FIG. 2, once the photophoretic trap 160 is actuated (i.e., turned "on"), other particles are prevented from entering the trap. This feature provides a way to achieve a trap-measure-release system that can measure one particle at a time, without other particles entering the trap during the acquisition of the spectrum of another particle. By contrast, in conventional tweezers traps, for instance, other particles in the airstream tend to be added continually to a trapped particle as its spectrum is being measured.

Figure 11:
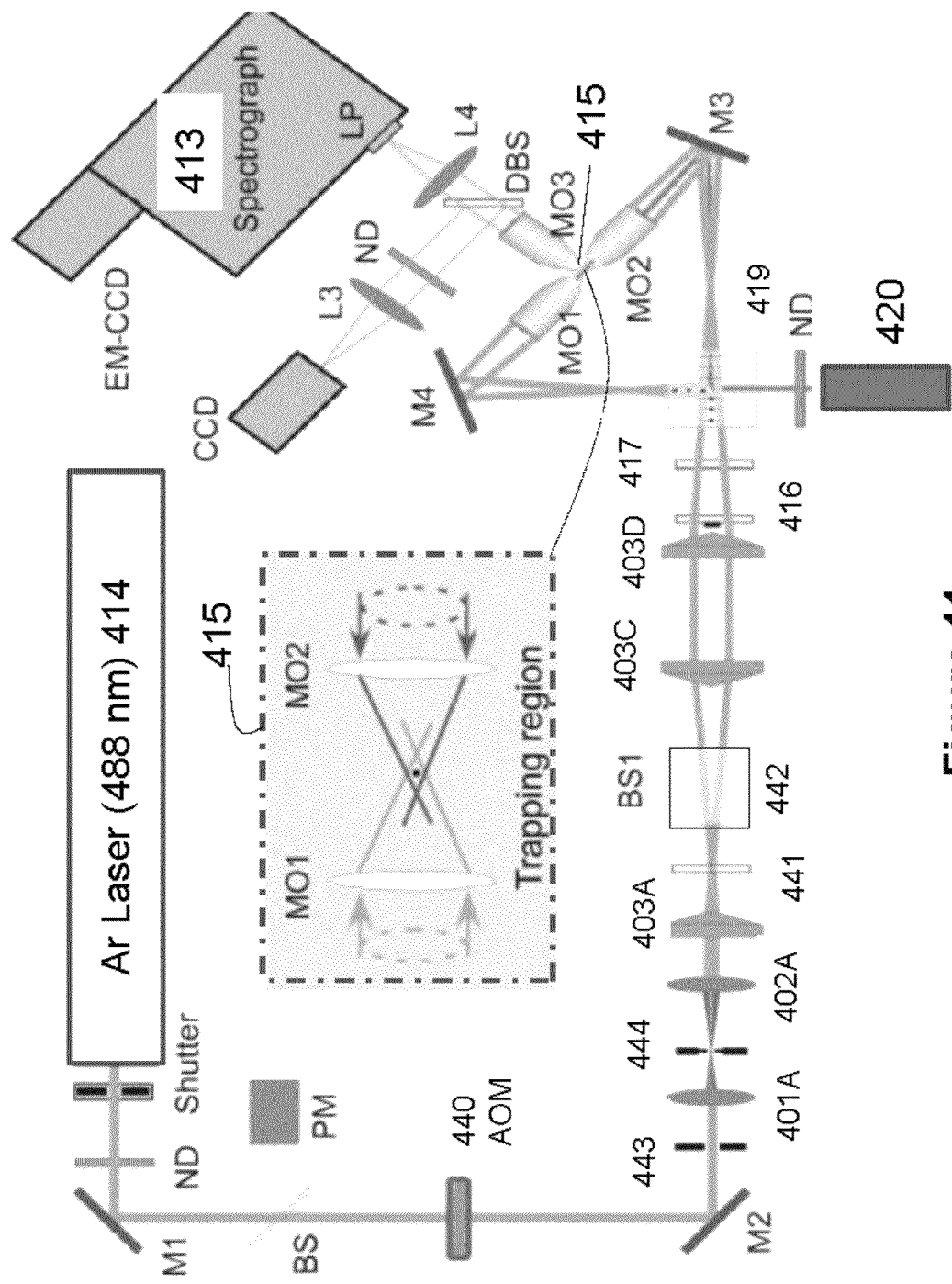
FIG. 11 illustrates photophoretic trapping and Raman measurement sub-systems for continuously sampling particles from air according to embodiments of the present invention.
Figure 12:
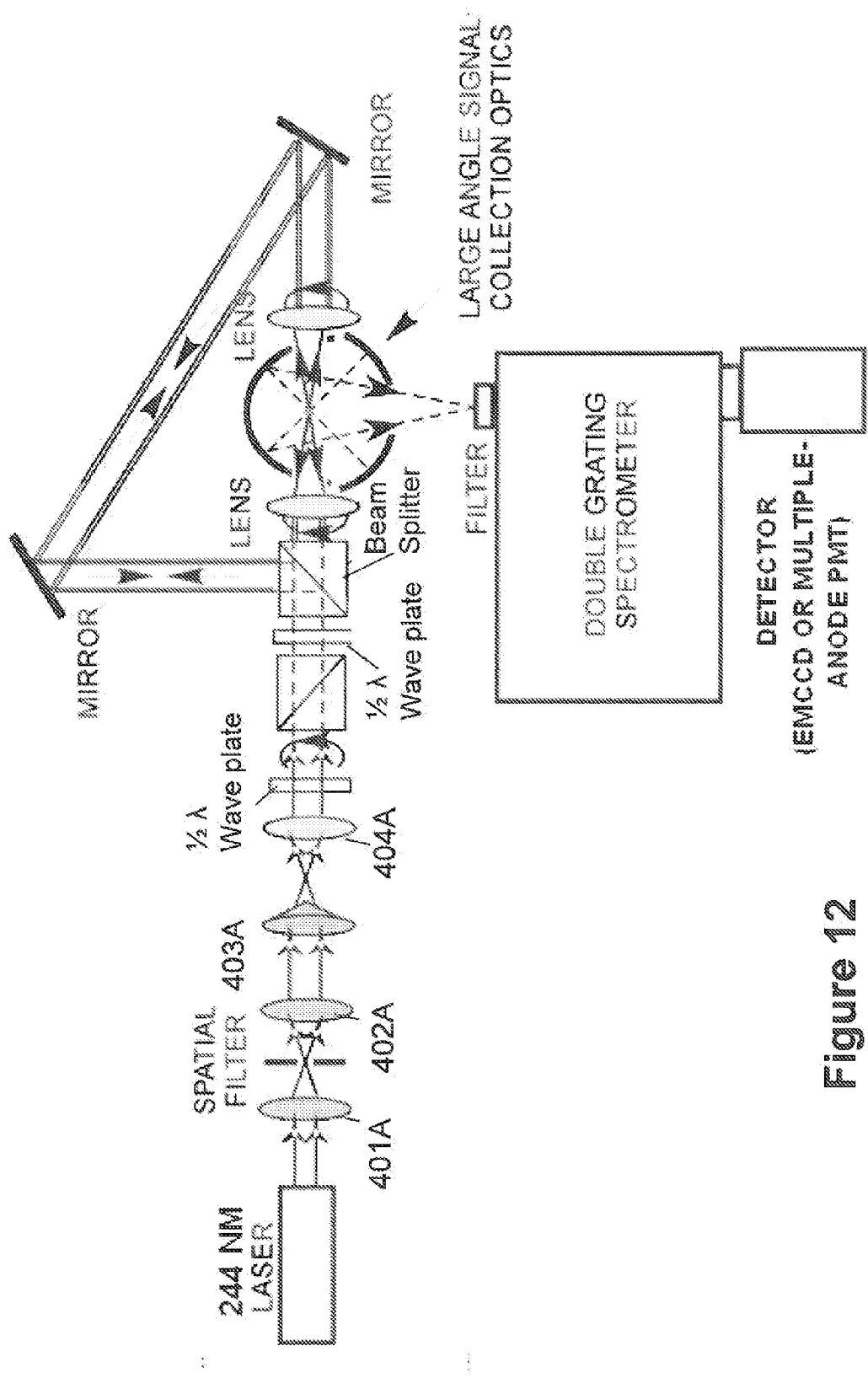
FIG. 12 illustrates photophoretic trapping and Raman measurement sub-systems for continuously sampling particles from air according to embodiments of the present invention.

The trapping laser 165 may be deactivated (e.g., turned "off" or blocked) so as to eliminate the photophoretic forces of the photophoretic trap 160, thus releasing the trapped particle 20.' The trapped particle 20' can then follow airflow 50 to exit the sampling volume 130 and ultimately the system 100 via outlet 110b. This may occur, for instance, after the particle's property is measured. Optics 167 are used to further manipulate the output of laser 156 so as to create the photophoretic trap 160. FIGS. 11 and 12 illustrate various optical elements that form optics 167 for two embodiments of the system, for instance.

While a particle 20' is trapped and held in the photophoretic trap 160, one or more properties of that trapped particle 20' may be measured or otherwise made.

A measurement device 170 thus is configured to measure at least one property of the trapped particle 20' while it is held in the photophoretic particle trap 160. These measurements may include, for example, Raman, fluorescence, thermal emission, laser-induced breakdown spectroscopy (LIBS), spark-induced breakdown spectroscopy (SIBS), elastic scattering over one, a few or many angles or wavelengths. The Raman, fluorescence, thermal emission, LIBS and SIBS may each be measured at one or more emission bands, including the case of sufficient bands to be considered a spectrum. The foregoing list is not exhaustive and other measurement techniques may be used. Devices for performing such measurements are generally known and will not be described in greater detail.

In one or more embodiments, Raman spectra (or Raman emission in one to several bands) of a trapped particle may be measured. Raman spectra provide information on the vibrational and rotational energy levels of molecules. These spectra can serve as "fingerprints" for various pure materials such as chemical warfare (CW) agent droplets, and may serve as fingerprints for some complex particles such as biological warfare (BW) aerosols prepared in certain ways, or certain species of fungal spores, etc. For these more complex particles such as those made from bacteria, the spectra tend to become more difficult to differentiate from spectra of similar bacteria grown under various conditions. More particularly, Raman spectral measurements may include, for example, Raman scattering, Raman spectroscopy, Resonance Raman spectroscopy, Coherent anti-stokes Raman scattering (CARS), and surface enhanced Raman scattering (SERS), which could be measured, for example, if the particles are combined with a droplet containing colloidal silver or gold nanoparticles before measurement).

Raman spectra may provide more information regarding the chemical and/or biochemical composition of individual airborne particles than can be obtained using ultraviolet laser-induced fluorescence (UV-LIF) even when the UV-LIF is combined with elastic scattering. According to one embodiment, the system may measure Raman spectra of particles at rates of 10's per minute to a few per second, depending upon the particle sizes, absorption coefficients, Raman cross sections, and concentrations of particles in air, etc.

In general, Raman emission is generated when excitation electromagnetic energy (light) interacts with the molecules in a material. This excitation light generates a spectrum of light that has a different (e.g., typically longer) wavelength than the wavelength of the excitation light. The Raman emission spectra are usually characteristic of the material and generally exhibit peaks at wavelengths which depend upon the excitation wavelength and the frequencies of vibration and rotation of the molecules in the material. Example Raman spectra measurements are shown in FIGS. 5 and 6 for various materials.

Figure 5:
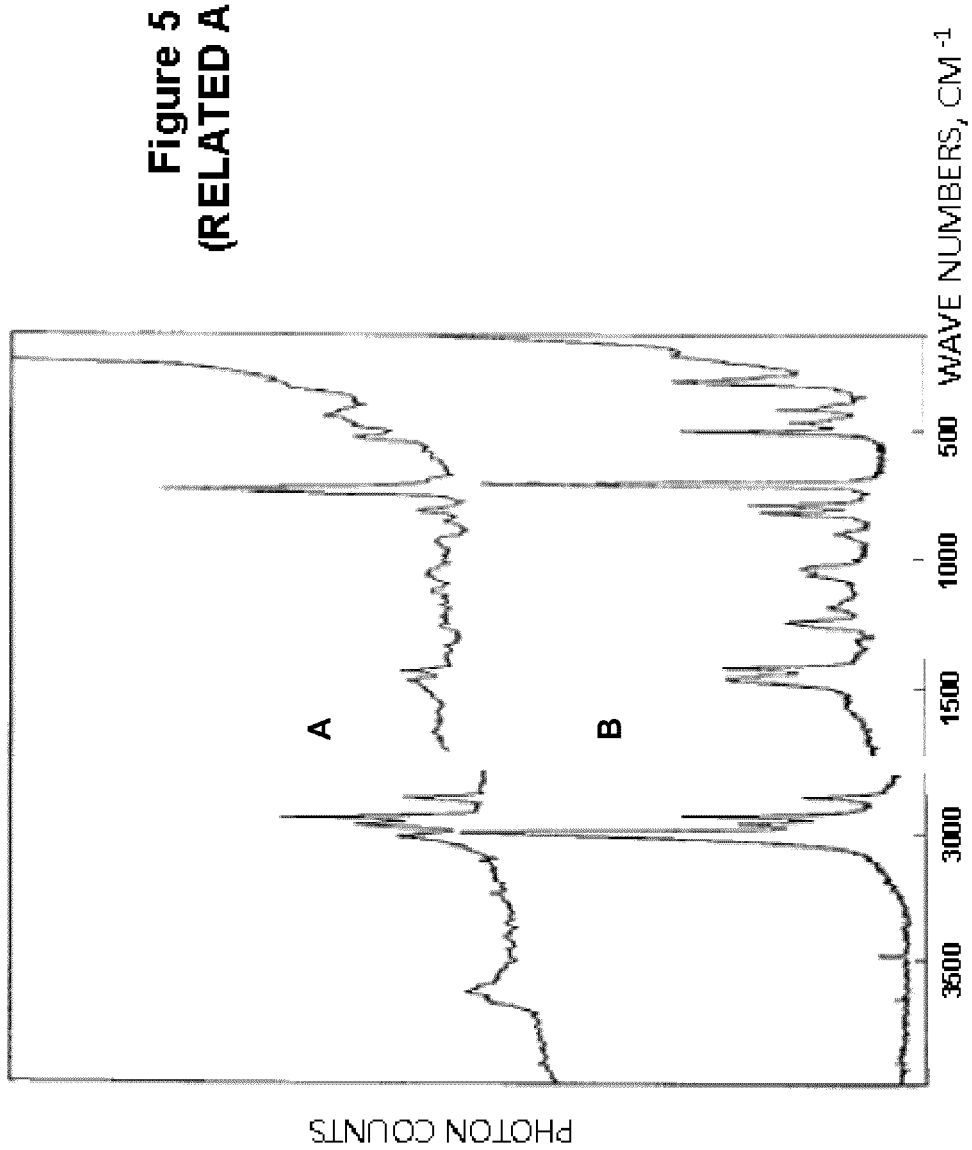
FIG. 5 illustrates exemplary Raman spectra of various substances.

FIG. 5 illustrates Raman spectra of a model insecticide, dimethyl methyl phosphonate (DMMP): (A) on montmorillonite clay; and (B) as the pure liquid as reported by J. M. Bowen et al., "Fourier Transform Infrared and Raman Spectra of Dimethyl Methylphosphonate Adsorbed on Montmorillonite," Environmental Science and Technology, 22, 1178-1181 (1988), herein incorporated by reference. For pure liquids, the Raman spectra of small molecules, such as DMMP, can be considered to be "fingerprints" because the peak positions and heights are so specific.

Because of their high information content, Raman spectra of particles trapped using conventional optical tweezers, including spectra of optically trapped individual biological cells (blood, yeast and bacteria), have been measured and used for various investigations, especially for particles in water. Raman spectra of samples airborne particles collected onto surfaces have been demonstrated to be useful for bio-aerosol pathogen characterization.

Figure 6:
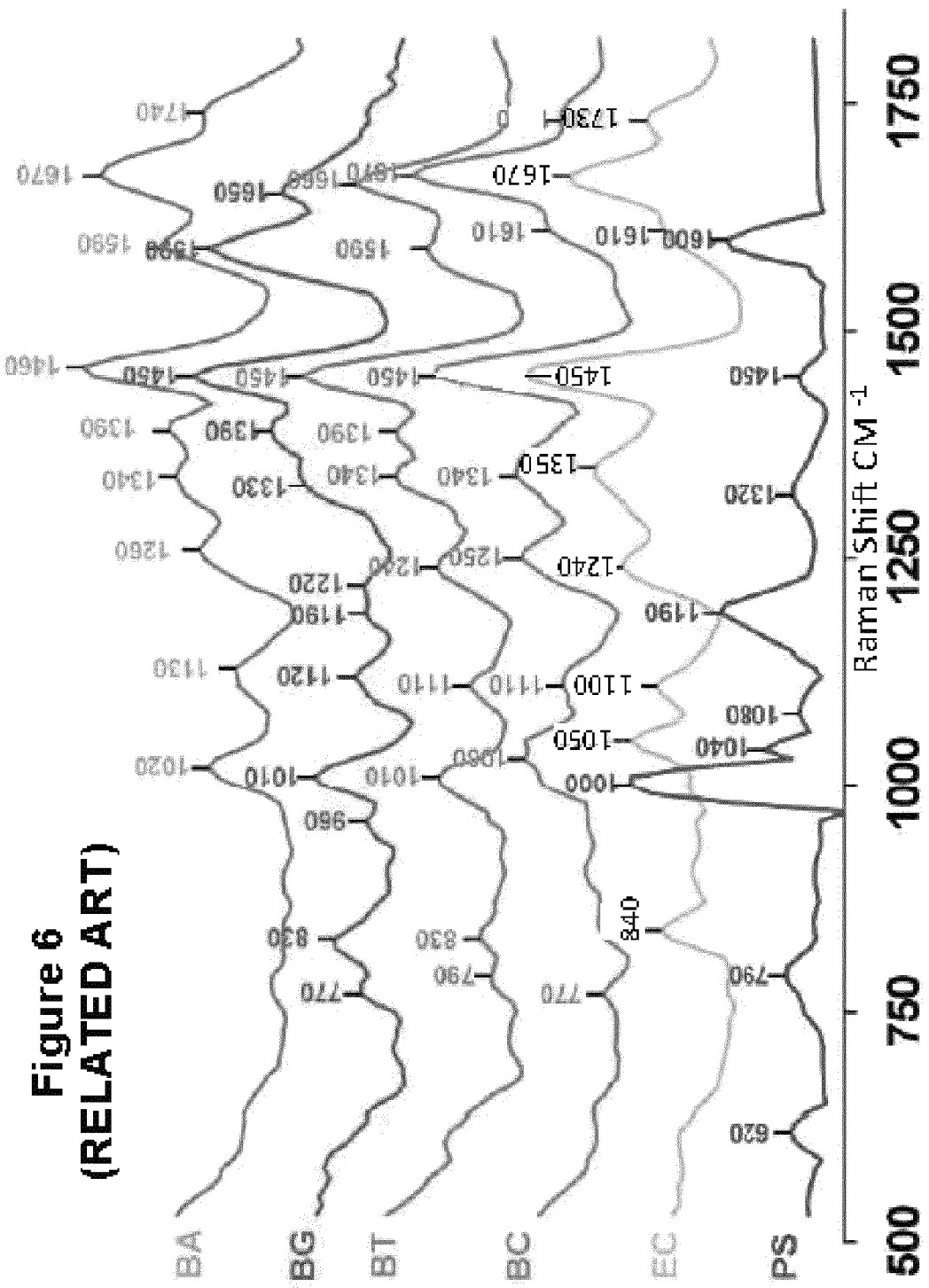
FIG. 6 illustrates exemplary Raman spectra of various substances.

FIG. 6 illustrates Raman spectra of *Bacillus anthracis* (BA), *Bacillus atrophaeus* (BG), *Bacillus thuringiensis* (BT), *Bacillus cereus* (BC), *Escherechia coli* (EC), and polystyrene beads (PS), as reported by A. Tripathi et al., "Bioaerosol Analysis with Raman Chemical Imaging Microspectroscopy," Analytical Chemistry, 81, 6981-6990 (2009), herein incorporated by reference. The spectra were measured for samples collected on a slide.

Typically, Raman spectra are obtained for particles collected on microscope slides or particles trapped in a liquid, allowing periods of seconds to minutes for signal accumulation. In liquid, most of the gravitational force is balanced by buoyancy forces, and the liquid viscosity prevents the aerosol particle from moving easily. Consequently, a relatively small radiation pressure force is sufficient for trapping particles in liquid and to overcome Brownian motion.

Measurements of Raman spectra of individual 1-μm diameter particles may require acquisition times on the order of a few milliseconds to many seconds, depending upon the particle composition, laser excitation wavelength, detector sensitivity, desired signal-to-noise ratio, the collection optics, and the stability of the particle during the measurement period.

To achieve a continuously (or quasi-continuously) operating air-sampling system in which no reagents, liquids, or cleaning or replacing of surfaces are required in measurements, the particles should be measured while trapped in air in a trap-measure-release system.

Holding particles in air during the time of the Raman spectra measurement allows the excitation laser beam and the collection optics to be optimized for that specific position of the particle in the trap, and therefore provides shorter acquisition times, lower requirements for laser power, and better signal-to-noise ratios.

Although Raman spectra may be used in some embodiments, it will be appreciated that other single-particle measurements are made on the particle, in addition to or as an alternative to Raman spectra measurements, in other embodiments. Depending on the property measurements desired, the emission, measurement, detection and analysis equipment may vary.

Returning to FIG. 2, at least one detector 172 may be included in the measurement device 170 for particle measurements. Typically in operation, only a fraction of the particles entering the system may be measured (although such operation is not limiting). The detector 172 can vary depending on which property of the trapped particle 20' is to be measured. General detectors and/or specific detectors may be used, for instance. In some embodiments, the detector 172 may include a spectrograph.

Depending on the measurement desired, an excitation source may be required generate energy which can produce emissions and/or another phenomenon by the trapped particle 20'.

In some embodiments, the same laser 165 that is used to trap the particle 20' may also be used to generate the excitation energy which causes the trapped particle 20' to generate the emissions and/or another phenomenon which is to be detected by the detector 172. For example, a portion of the beam of laser 165 may be split off from the rest of the beam (e.g., with a mirror, beamsplitter and/or other optics), manipulated and directed via optics to the trapped particle 20'.

In other embodiments, increased flexibility in trapping and measuring can be obtained by using one or more separate excitation sources 174. These sources, such as a laser, may be provided in the measuring device 170 that are configured to excite emissions of the trapped particle. As such, the trapping laser 165 need not be used in the measuring process. The excitation sources 174 may be operated at a different wavelength and/or other parameters than the trapping laser 165. For example, in some embodiments, the excitation sources may be focused tightly or weakly, depending on the application or mode of operation.

A multiple-laser system may be advantageous for trapping both absorbing particles and non-absorbing particles. Absorbing particles are trapped using photophoretic forces as described above. Particles with little or no absorption are trapped using the radiation pressure forces generated by another tightly focused laser beam to form a laser-tweezers trap. The wavelength of the second laser beam may be chosen to be one that is not absorbed well by the particle. In addition, a multiple-laser system can be used to controllably excite the emission at whatever excitation wavelength is desired. For instance, a first laser may be used for trapping as described above. If the first laser, with a wavelength chosen to trap the desired absorbing particles, generates too much fluorescence, a second laser can be chosen so that its Raman emission is at wavelengths, e.g., longer than 800 nm, where the fluorescence interference is much weaker. If the second laser is at a wavelength that is not absorbed by the particles of interest, it can be focused tightly to the center of the trapping region and can contribute to trapping these non-absorbing particles of interest. If the second beam were at a wavelength that is absorbed by the particles of interest, its intensity is kept low enough that it does not push particles out of the trap. Once a particle is trapped, the intensity of the second beam is increased so that the Raman spectrum is measured more rapidly. One specific example of such an approach is to use the relatively inexpensive 488-nm light to trap the particles, but use the more expensive 244-nm light (the doubled frequency if the fundamental is 488 nm) to excite the Raman emission in a region where the fluorescence problem can be avoided. Another example application is to generate both the trapping and the Raman-excitation beam from one laser (e.g., at 244 nm), using a beamsplitter and a means to control the amplitude of the second beam (the Raman-excitation beam).

Figure 7:
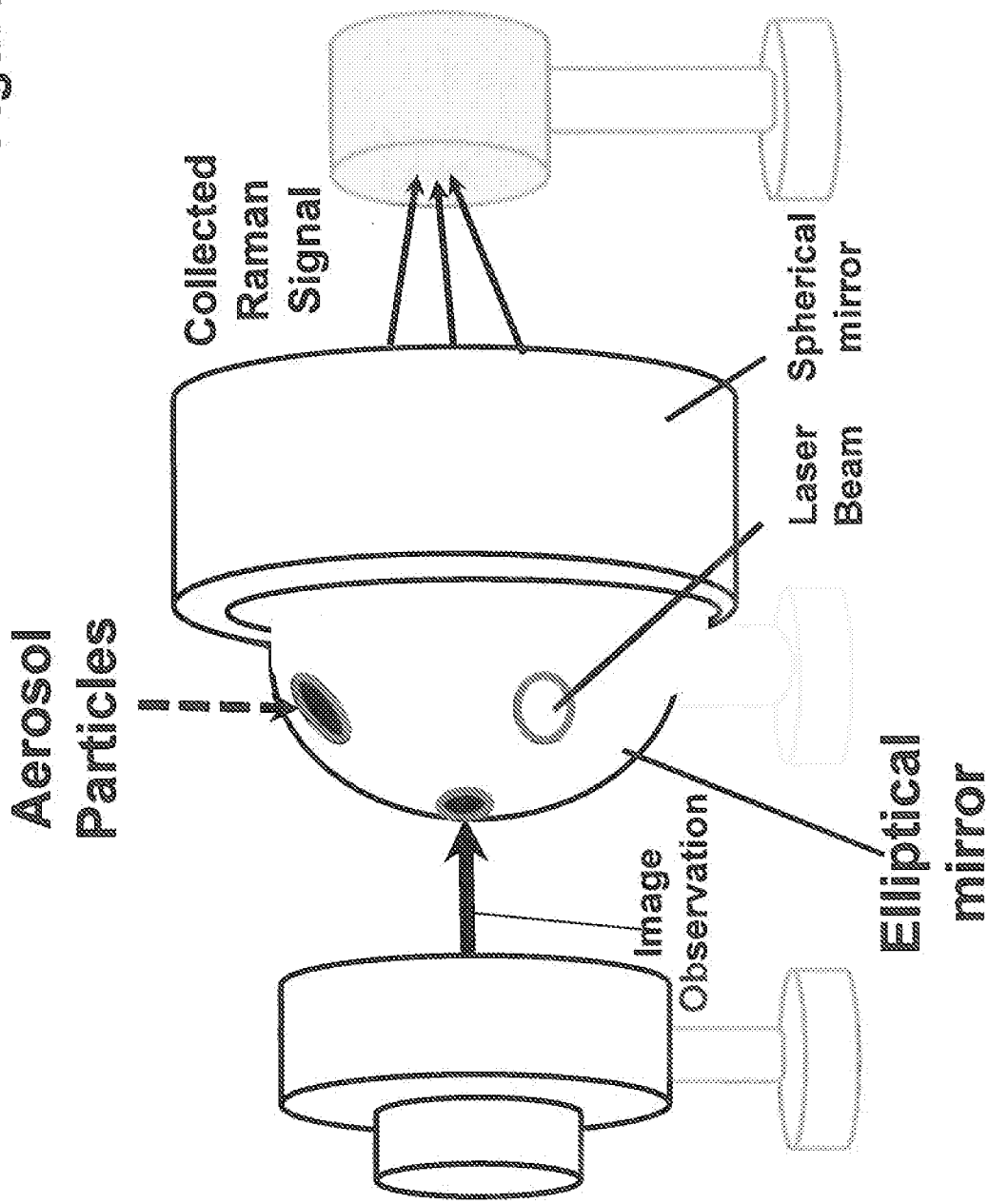
FIG. 7 shows one configuration of collection optics which may be used in embodiments of the present invention.

Collection optics 176 may further be included for manipulating emission and/or phenomenon to be measured by detector 172. FIG. 7 shows one configuration of optics 176 adapted for collecting the Raman spectral signal over a large solid angle using a combination of an elliptical mirror and a spherical mirror according to embodiments of the present invention.

These optics generally include an elliptical mirror and a spherical mirror. The aerosol particle will be trapped at one of the focal points of the elliptical mirror, which has been positioned to coincide with the center of the spherical mirror. Therefore, light that reaches the spherical mirror from the particle is reflected back to the center of the mirror and towards the elliptical mirror, while light that reaches the elliptical mirror either directly from the particle or reflected from the spherical mirror is reflected to the second focal point of the elliptical mirror. This second focal point overlaps with the entrance of the spectrometer. This configuration enables collection of a large solid angle (e.g., greater than $2\pi$ or even $3\pi$ sr) of the Raman spectral emission from single particles, and it focuses the emission into a small angle to match the f-number of the Raman spectrometer.

Returning to FIG. 2, a particle analyzer 180 is configured to analyze the measurement data. More particularly, the analyzer 180 may rapidly identify, determine, classify, characterize and/or sort, particles according to their measured properties. In some embodiments, it may determine, from at least one measured property, a parameter related to the trapped particle 20'. This may include determining from the measurements one or more parameters related to particle shape, size, refractive index, absorption, Raman cross section or any combination thereof of the trapped particle, for example. Parameters may be determined or otherwise computed from measured data. For instance, extracting the size, shape and refractive index of a particle from angular scattering measurements requires solving an inverse problem, or at least finding an approximation to that solution.

The particle analyzer 180 may be configured to monitor measurement data for potentially harmful particles such as bacteria, bacterial spores, pollens, fungal spores, protein allergens, smoke particles, and pollutants, such as pollutant particles that contain polycyclic aromatic hydrocarbons or reactive oxygenated species. A database (not shown) of known threats may be searched and/or analyzed with respect to measurement data, for example. Also, past measurements may be stored for further analysis and/or future searching.

In some instances, the particle analyzer 180 may be used to count and classify particles which can be used to determine or estimate exposures of persons to various airborne chemicals and pollutants, such as, for example, smoke from fires or burn-pits, or to diesel exhaust.

The particle analyzer 180 may be a computer or microprocessor, for instance, which is configured to execute an algorithm 182 that is used to identify and or classify particles based on their measured properties, preferably in real time. The different categories can correspond to one or more different pollens, bacteria, bacterial spores, allergens or any other classification scheme. In some embodiments, the near-real-time algorithm used to classify particles into categories will be similar to those described in papers by R. G. Pinnick et al, "Fluorescence spectra of atmospheric aerosol at Adelphi, Md., USA: measurement and classification of single particles containing organic carbon," Atmos. Environ., 38, 657-1672 (2004); and by Y. L. Pan et al, "Single-particle laser-induced fluorescence spectra of biological and other organic-carbon aerosols in the atmosphere: measurements at New Haven, Conn., and Las Cruces, N. Mex.," J. Geophys. Res., 112, D24S19, 1-15 (2007), each of which is herein incorporated by reference. In other embodiments the near-real-time algorithm used to sort particles into categories may be the one described by Y. L. Pan et al, "Fluorescence spectra of atmospheric aerosol particles measured using one or two excitation wavelengths: Comparison of classification schemes employing different emission and scattering results," Optics Express, 18(12), 12436-12457 (2010), herein incorporated by reference. Of course, for the case of Raman spectra the algorithms may be the same or similar, but the actual spectral shapes for the different particle categories are very different, and generally will have higher information content. Again, for the case of thermal emission the algorithms may be the same as or similar to those described above, but the actual spectral shapes and spectral features that are used in the algorithms are different.

Additionally, the particle analyzer 180 may be coupled to a warning detector 184 that is configured to provide a warning when particles consistent with expected or known biological or chemical agents are detected. This may be instrumental, for instance, in the case of an attack with aerosolized biowarfare or chemical warfare agents by indicating a potential attack, so that personnel can begin to take protective actions. The warning detector 184 may include an audible alarm or siren, flashing (strobe) light, display screen, etc. which can provide audible and/or visual warnings. In some instances, written instructions may be provided by the display screen or printer for the aid of personnel. If the system is connected to a network (e.g., phone, internet, intranet, etc.) it may generate messages to contact first responders or other emergency personnel, command personnel and/or other persons, as desired.

A particle sorter 190 can physically sort, and optionally store, particles based on their measured properties. One particle sorting system which may be used with embodiments of the present invention is disclosed, for example, in U.S. Pat. No. 7,410,063, herein incorporated by reference. In other embodiments, once it is determined that a trapped particle should be collected and stored for further analysis, the air surrounding the particle is drawn though a filter (e.g., glass fiber, or filter with small holes (e.g., a nucleopore, or Millipore filter) by opening a valve connected to a vacuum or by turning on an air pump, and then catching the particle on the filter as the air it is entrained in is drawn through the filter.

A controller 200 is provided which is configured to the various control operations of the system 100, preferably in a fully-automated manner so that the system can trap a particle from air, hold it for as long as needed to measure its Raman spectrum or other properties as appropriate, then release the particle once the measurement(s) are completed, and then continuously repeat these steps (trap, measure, release). The controller 200 may be a computer or microprocessor, for instance, that includes computer-executable code which when executed is configured to implement methods for continuously sampling particles from air.

The controller 200 may be configured to generate and send signals to the various elements described herein, for instance, causing the elements to function or be otherwise actuated/deactivated upon command. This may include generating signals to: trap a particle in the sampling volume and hold the trapped particle; measure a property of the trapped particle; and release the trapped particle. The aforementioned sequence may be repeated as many times as desired.

Operation of the system 100 may vary depending on the particle detector 150, as discussed above. For example, in one embodiment, the controller 200 may generate a signal to actuate the photophoretic trap 160 to trap the particle in the sampling volume 130 based on a detection signal received from the particle detector 150. Or, in another embodiment, the controller 200 may generate a signal to cause the measuring device 170 to measure a property of a trapped particle 20' already trapped in the photophoretic trap 160 based on a detection signal received from the particle detector 150.

Once a particle is trapped by the photophoretic trap 160, depending on the desired operation, controller 200 may ensure that it is held for sufficient time in order to: a) make one or more measurements of the same particle using different techniques; b) make improved measurements because the particle location can be better defined; and c) make measurements of dynamic processes in a trapped particle, by repeatedly measuring the spectrum or other parameter to see how it changes with time. In one embodiment, the fluorescence spectra can be measured with higher resolution, and the angular optical scattering can be measured with far better knowledge of the position of the particle and of the angles of the measured scattering intensities. The resulting reduction in uncertainties in the measurements makes the inverse problem, to extract parameters relating to the shape, size or chemical composition, far more tractable. Other sampling methodologies may also be executed, and the aforementioned ones should not be thought of as exhaustive.

Figure 8:
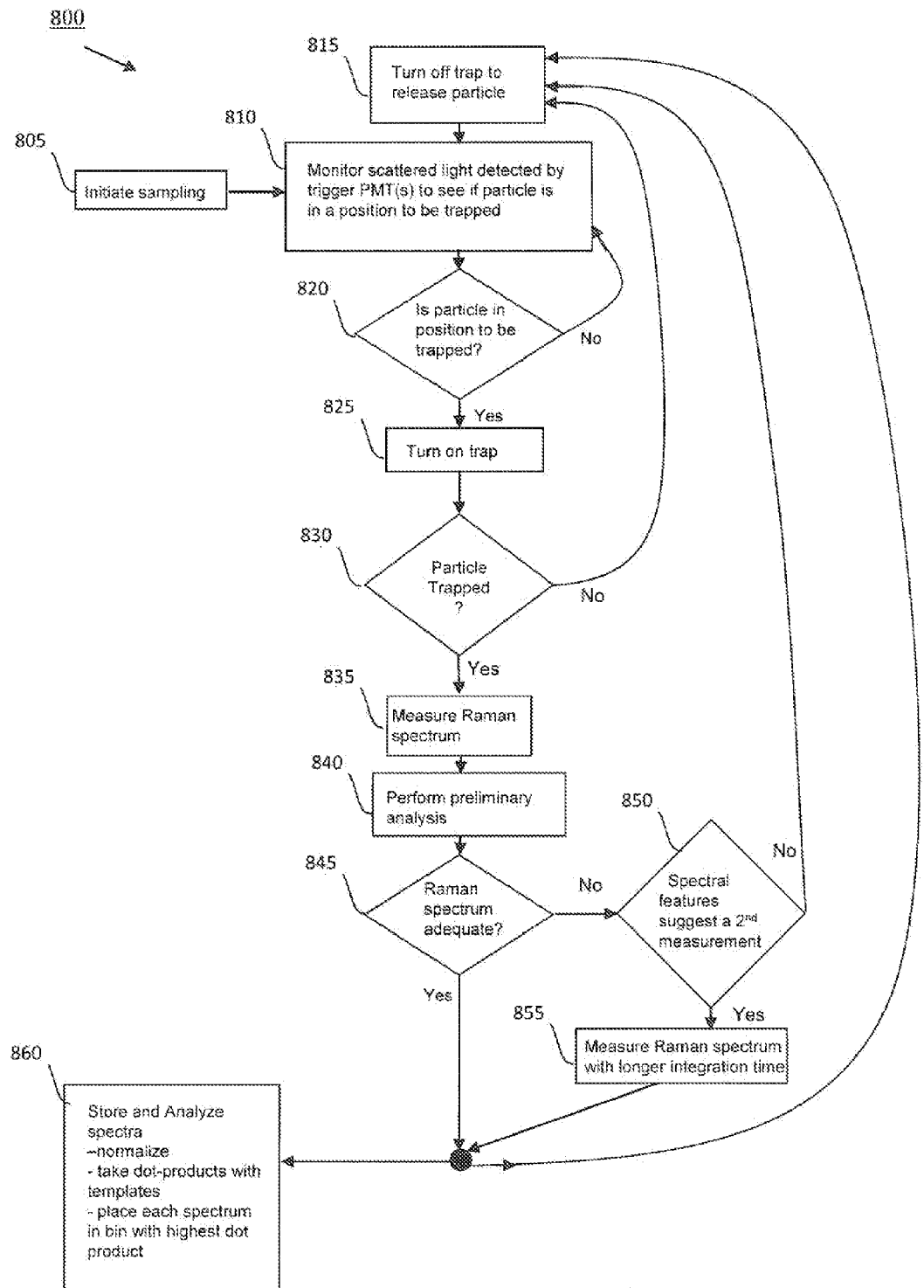
FIG. 8 illustrates the logic for the controller according to one embodiment of the present invention.

FIG. 8 illustrates the controller logic 800 for the controller 200 according to one embodiment. Controller 200 may include one or more processors to implemented controller logic 800. It could be dedicated hardware like an application-specific integrated circuit (ASIC) or a field programmable gate array (FPGA), software, or a combination of dedicated hardware and software.

The controller 200 initiates sampling in operation 805 and monitors the voltage output of the one or more PMT assemblies which measure the forward elastic light scattering from particles passing through the one or more diode-laser trigger beams in operation 810. A subsystem of the controller includes the pulse-shaping amplifiers typically set with time constants of one to a few microseconds, and includes single channel analyzers which operate as discriminators in window mode, and, if two diode-laser-PMT assemblies are used, includes an AND gate to send an output signal when both of the single-channel analyzers provide an output signal indicating that both the PMTs have measured optical scattering that is above threshold, all as described in Chang, Pan, Pinnick and Hill, U.S. Pat. No. 6,532,067 B1, and illustrated in the lower part of the first figure of that patent, herein incorporated by reference. One significant difference between U.S. Pat. No. 6,532,067 and the present invention is that in U.S. Pat. No. 6,532,067 the air flow rate is approximately 10 meters/second (m/s), which is acceptable when trapping of particles is not required, while in the present invention the velocity of the airflow, and particles carried in the airflow, it is far smaller than 10 m/s, typically less than 1 m/s, and can be less than 1 cm/s, for particles that are more difficult to trap because of low optical absorption, high-thermal conductivity or small size, for example, less than 1 µm.

In operation 820, a determination is made if there is a particle in position to be trapper. If the AND gate (See U.S. Pat. No. 6,532,067 B1, FIG. 1) emits a signal indicating that both PMT voltages exceed a preset threshold or to fall within a preset window (set so as to select and measure particles within a desired size range), and so a particle is in the intersection of the two trigger beams, then the controller turns on the trap in operation 825 (for example, causes the laser to be unblocked by changing the voltage applied to an acoustooptic modulator), typically within fractions of a millisecond, so that the particle can be held within the trapping volume and other particles can be prevented from entering that trapping volume, so that a substantially single-particle measurement can be obtained. Note that within 0.5 ms a particle moving at 5 cm/s moves 25 µm, so the intersection of the trigger laser beams could essentially overlap the trigger volume and the detected particle would in the large majority of cases still be within the trapping volume when the trapping laser was turned on.

In operation 830, after the trap has been on for a short time, e.g., 1 ms to 10's of ms, in order to give the trapped particle time to move to near the center of the trap, the controller examines the amplified voltages from PMTs which record the elastic scattering from any particle caught in the trap to ensure that a particle has in fact been trapped. In one preferred embodiment, the diode-laser(s), PMT(s) and electronics assembly used to verify a particle is trapped are the same as those used for the initial detection of the particle (that is the trigger laser-detector assembly).

If the amplified voltage(s) from the PMT(s) detecting trapped particles do not exceed a preset threshold, the controller takes this as an indication that no particle was trapped and so the trap is turned off (in operation 815, top of FIG. 8) and the trigger laser/PMT subsystem begins looking for a particle in, or moving into, the trapping volume in operation 810.

On the other hand, if the amplified voltage(s) exceed a threshold, the controller takes this to indicate a particle, and the signals for the Raman measurement system to measure the Raman spectrum of the trapped particle in operation 835. The controller may also send to the data acquisition system for the Raman spectrum measurement the length of time for which to acquire the Raman spectrum. This desired acquisition time is determined from the voltage(s) from the PMT(s), and a set of times required for Raman spectrum acquisition which is determined using calibration particles of the desired type(s) to detect and for sizes within a desired range of particle sizes.

Once the Raman spectrum is recorded, in operation 840, the spectrum is rapidly analyzed to determine if it is consistent with Raman spectra of particular particles of interest or otherwise adequate in operation 845. For example, in the operation, the controller may determine whether the Raman spectrum has a signal to background ratio that suggests it should be helpful to record the Raman spectrum a second time with a longer integration time in operation 850.

If that is the case, the controller signals the Raman system to acquire this second Raman spectrum with a longer acquisition time in operation 855. If that is not the case (e.g., because the spectrum appears adequate, or because it appears hopelessly noisy) then the particle is trap is turned off in operation 815, the particle is released, the sampling cycle repeats again in operation 810.

Further analysis of the spectrum and recently measured spectra continues concurrently, and the spectra are stored for analyzing in operation 860. If the measured Raman spectra are consistent with particular types of harmful particles, that information is transmitted to any desired locations.

In a simpler embodiment of the controller, there may be no immediate analysis of the spectrum to ascertain whether a second Raman spectrum will be recorded. Instead, as soon as the Raman spectrum is recorded, the particle is released and the trigger subsystem begins monitoring for a particle moving into the trapping volume.

Figure 9:
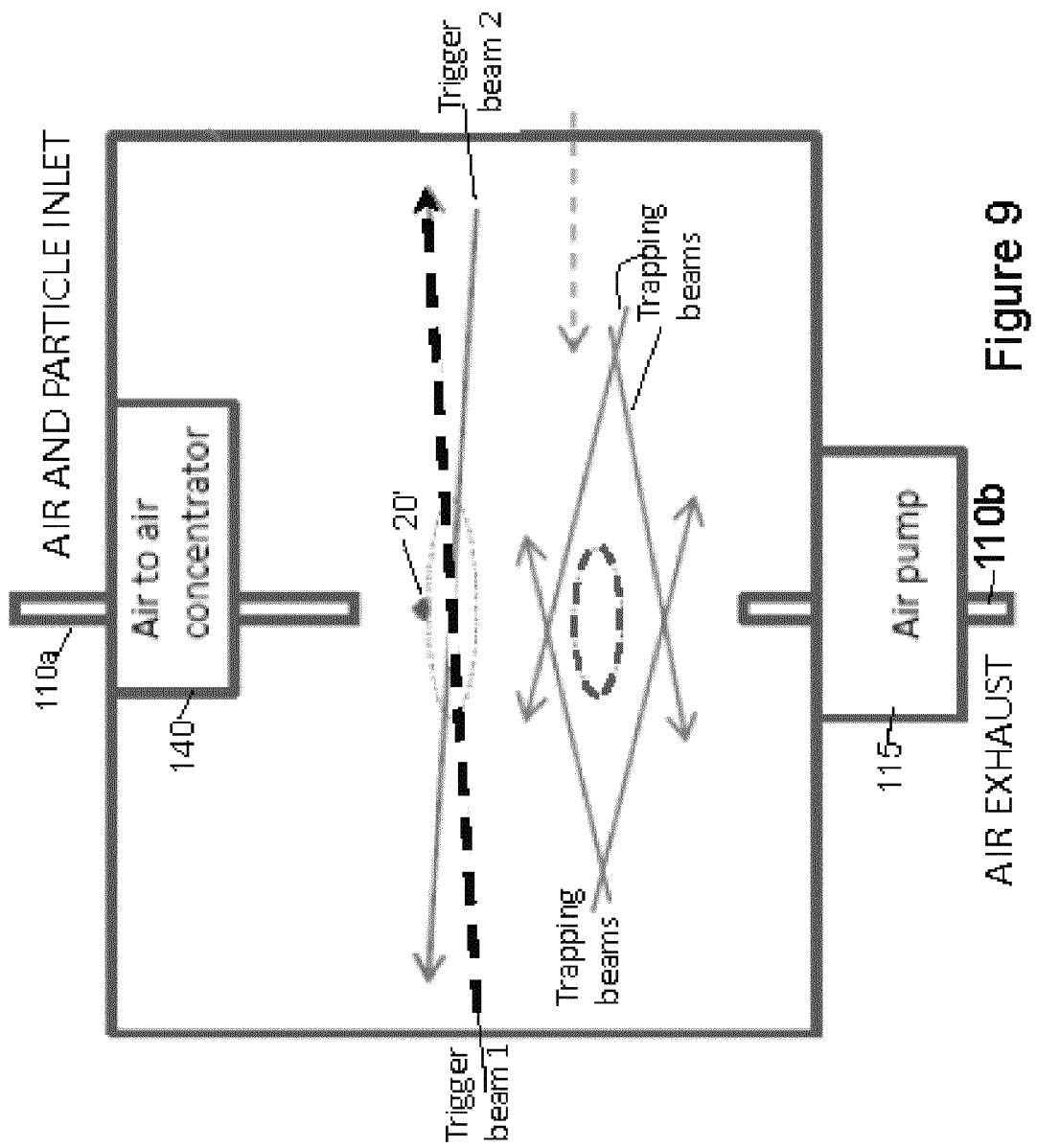
FIG. 9 illustrates a schematic of the air sampling and particle trapping part of a single particle Raman spectrometer system according to an embodiment of the present invention.
Figure 10:
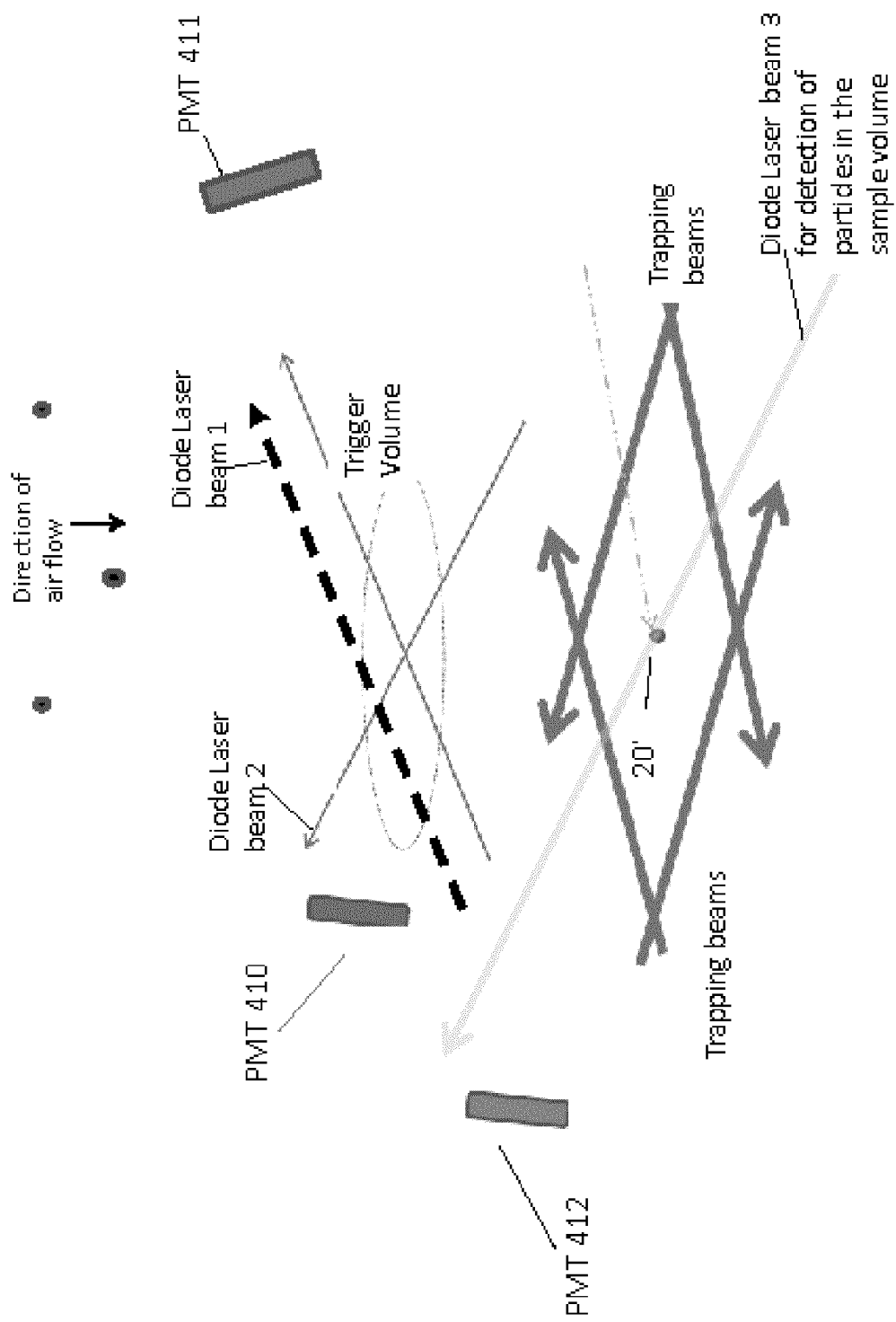
FIG. 10 illustrates a schematic of a photophoretic trap and trigger beams with detectors according to an embodiment of the present invention.

FIG. 9 illustrates a schematic of a single-particle Raman spectrometer system according to an embodiment of the present invention.

Here, particle laden air is drawn into an airtight box through an inlet 110*a*, and is drawn out of the box through an air pump 115, and then exits through the air exhaust outlet 110*b*. In this embodiment the aerosol entering the box passes through an air-to-air concentrator which increases the particle concentration in order to increase the sample rate. As illustrated in FIG. 9, when a particle 20' scatters light from both trigger beams, then that particle must have passed through the intersection of the two beams. In the lower part of the box the counter-propagating arrows represent a cross section of two hollow conical beams which intersect to form a low-intensity region surrounded by high-intensity beams. When a particle is detected approaching the trapping volume (inside the dashed oval, inside the volume defined by the conical beams, the beams are turned on and the particle is trapped so that its spectrum can be measured.

FIG. 10 is a highly schematic drawing of a photophoretic trap and trigger beams with detectors according to an embodiment of the present invention. In FIG. 10, a particle is shown in the sample volume. After this particle's Raman spectrum is measured, the trapping laser beam is blocked (in this embodiment the AOM (not shown in 10 because it would be off the page) deflects the beam so that it travels to a beam block instead of to the trapping region), and so the trapped particle is no longer held, and so is carried out of the sample volume in the airflow. When the next particle is in the trigger volume it scatters light from both trigger lasers, and this light is detected by PMTs 410 and 411. The time at which the particle is detected, along with the airflow rate and position of the trigger beams relative to the trapping volume, are used to determine the appropriate time to unblock the trapping laser (i.e., the AOM is turned off so that it does not deflect the beam), so that the detected particle is trapped and its Raman signal can be measured. Shown in FIG. 10 are PMTs 410, 411, and 412. PMT 410 detects scattering from diode laser 2. PMT 411 detects scattering from Diode laser 1. PMT 412 detects scattering from diode laser 3.

In FIG. 10, a particle is shown in the sample volume. After the particle's property (e.g., Raman spectrum and/or other property) is measured, the trapping laser beam is blocked such that the trapped particle is no longer held and so is carried out of the sample volume in the airflow. For example, an AOM may deflect the trapping laser beam so that it blocks it.

When the next particle enters the trigger volume it scatters light from both trigger lasers. This light is detected. The time of detection is used to determine when to unblock the trapping laser, so that the detected particle is trapped, so that its Raman signal can be measured. For instance, the AOM may be turned off so that it does not deflect the trigger beam.

The two beams are focused to form hollow conical beams which overlap to produce a biconical region of low intensity surrounded in any direction by the high intensity regions of the hollow beams. This photophoretic trap is stable for absorbing particles. With this trap, Raman spectra or other properties can be measured from individual particles in air such as, for example, micron-sized clusters of multi-walled carbon nanotubes (MWCNTs) and Johnson grass smut spores (a fungal spore). Particles remain trapped because gravitational, drag, and other forces are not sufficient to exceed the photophoretic trapping forces.

FIG. 11 illustrates the trapping and Raman measurement subsystems for a system for continuously sampling particles from air according to an embodiment of the present invention. These subsystems, however, do not include the subsystems for detecting particles approaching or entering the trap or rapidly gating the trapping system on or off. Therefore, in the examples and results shown in FIGS. 11 and 13-15, the particles were aerosolized by turbulent airflows from an ultrasonic needle or from a can of compressed air. These rapid airflows initially generate high drag forces on the aerosol particles and thereby accelerate the particles. The combination of high momentum and high drag forces can exceed the barrier posed by the trap, and so the particles can enter the trap. Once the generation of these turbulent airflows stops, the airflow and particle velocities decrease and can change directions, as do the drag forces on a particle. Therefore, the velocities and drag forces that were able to push a particle into the trapping region can change direction and/or decrease in magnitude sufficiently that the drag forces are unable to push the particle out of the trap.

In FIG. 11, the trapping region is formed by two counter-propagating hollow conical beams (see inset in the middle). ND: neutral density filter; M: mirror with high reflection at 488 nm; BS: beam splitter; PM: power meter; DP: diaphragm; L: lens; MO: microscope objective; DBS: dichromatic beam splitter; LP: long-pass filter; Light from the laser 414, after being reflected by mirror M1, passing through the beam splitter and the acoustooptic modulator 440, and reflected by mirror M3, enters beam expanders 401A, 402A. Light from the beam expanders enters the axicon lens 403A and is focused by focusing lenses 404A, onto Axicon lenses AL2, AL3 as shown in FIG. 11. The AOM 440 is used to rapidly turn the trap on or off, by rapidly deflecting or not deflecting the beam passing through it.

The light source 414 is a continuous-wave (cw) argon ion laser operating at 488 nm (Coherent Inc., Innova 300C FreD). It produces a linearly polarized Gaussian beam (TEM00). Its output power can be controlled by adjusting the plasma tube current, and/or by adjusting a neutral density filter. The laser beam is cleaned and re-collimated using a 2-mm-diameter diaphragm 443, two lenses 401A and 402A (where 401A has a focal length of 25 mm, and 402A has a focal length of 50 mm), and a 400 μm diameter pinhole 444. The Gaussian beam is transformed into a hollow beam by passing it through three axicons 403A, 403C, 403D (Thorlabs, cone angle 176°) and a spatial filter 416. The spatial filter 416 is an optical window with a 5-mm mirror at the center for blocking the remaining light along the optical axis. The first half-wave plate 441 and polarizing beam splitter 442 are used for fine adjustment of the laser intensity. The second combination of wave plate 417 and polarizing beam splitter 419 is used to separate the laser beam into two equal intensity beams propagating perpendicularly to each other, where one is polarized horizontally and the other polarized vertically. The different polarizations for these two beams are not required for generating the desired optical intensity distribution for trapping the particles, but are designed to make the two equal-intensity beams travel around the triangular path only once, then exit at polarizing beam splitter 419, in order to minimize unwanted multiple reflections and interference patterns. The two beams are further made to overlap as they propagate in opposite directions, and (initially) to focus to a similar point (equidistant from polarizing beam splitter 419) by microscope objectives MO1 and MO2 (Nikon, ELWD 20×, NA=0.4). Each MO is mounted on a 2D tiltable frame supported by a 3D translation stage, for ease in alignment. By moving MO1 and MO2 towards each other at least 10 μm (50 μm for the measurements shown here) along the optical axis longitudinally, a hollow biconical region with two closed ends is formed for particle trapping (see the inset of "trapping region" 415 at the center of the figure).

A continuous wave diode laser 420 operating at 635 nm is used to illuminate the trapped particle for alignment. MO3

(Creative Devices, f=20 mm, 50×, N.A.=0.42) collects both the Raman scattering signal and the elastic scattering from the trapped particle. The dichroic beam splitter (DBS, Semrock LPD01-488RU-25) reflects the 488-nm light and transmits the 494.3- to 756.4-nm band (>95%) for a 45° incident beam. Another long pass Raman edge filter (LP, Semrock LP02-488RE-25) further blocks the residue of elastic scattering from the laser with high transmission in the 491.2-1110.8 nm band (>95%). The scattering image of the trapped particle is monitored by a CCD camera (Pulnix TM-9701) for the 488-nm scattering, and by an Electron Multiplying CCD (EM-CCD, Princeton, ProEM 1600×200), operating in imaging mode, for the 635-nm scattering. This back-illuminated, UV-enhanced EMCCD detector has the combined advantages of traditional charge-coupled devices (CCDs) and image-intensified CCDs (ICCDs), and has a quantum efficiency of about 90% in visible and above 35% in UV. The Raman signal is dispersed by a spectrograph (Acton, SP2300, grating 1200/mm, blaze 500 nm), and recorded by the EMCCD in spectroscopy mode.

FIG. 12 illustrates a similar system for continuously sampling particles from air according to an embodiment of the present invention. In FIG. 12, the collection solid angle for the Raman emission is very large, and could be greater than $2\pi$ steradians. In FIG. 11, the system includes a diode laser directed into the sampling volume. This diode laser can be used to detect if a particle is in the sampling volume or to excite the Raman emission.

Figure 13:
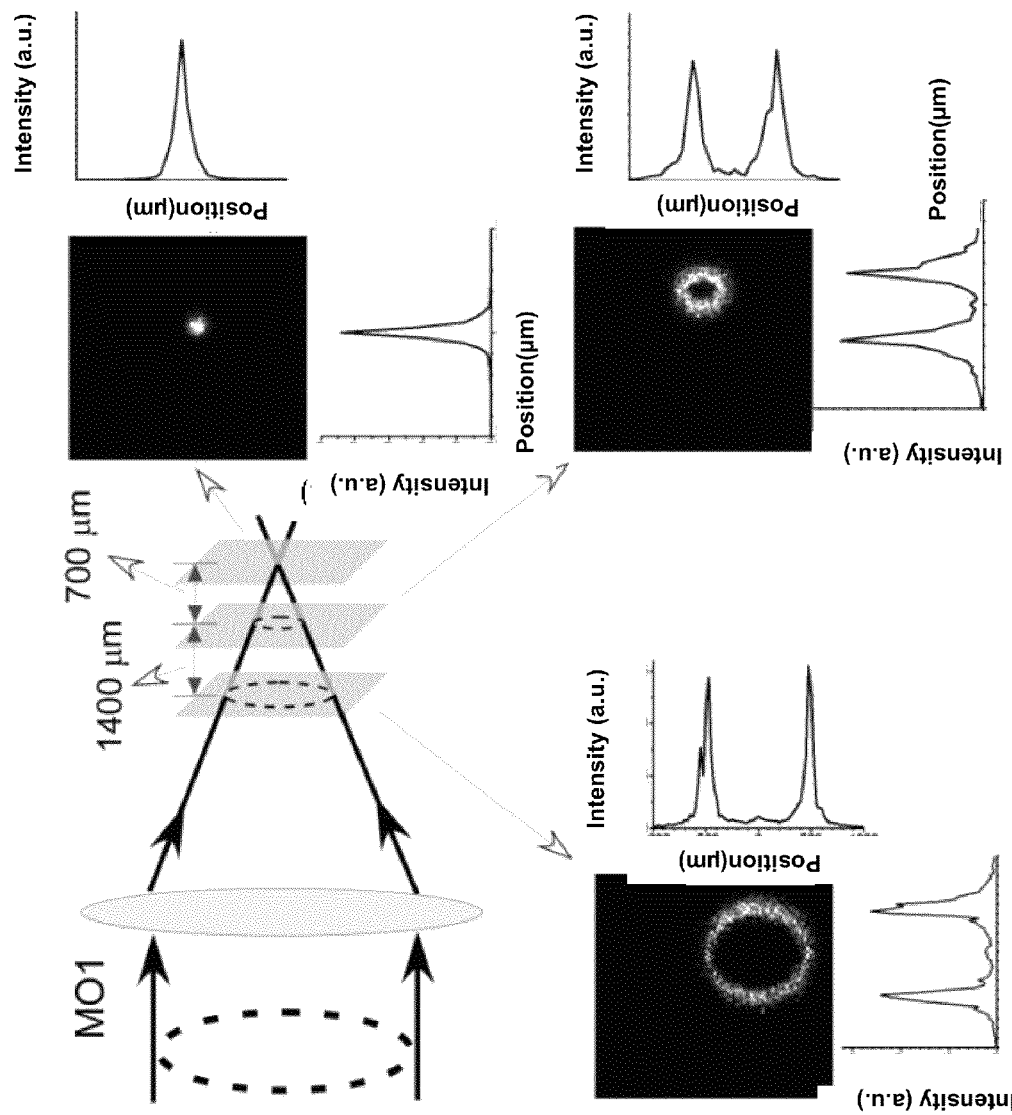
FIG. 13 illustrates the light intensity distribution for one of the conical beams, shown in a plane transverse to the axis of the conical beams of the system illustrated in FIG. 10.
Figure 14:
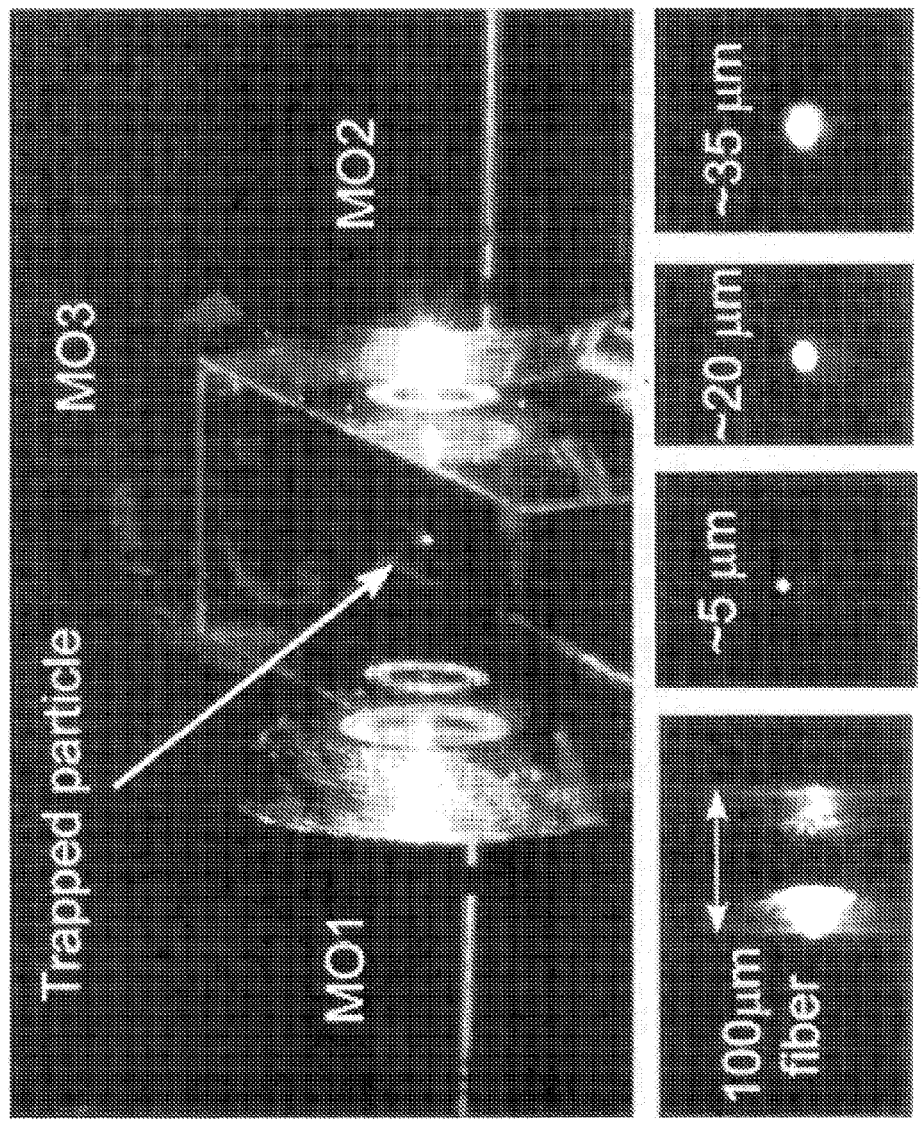
FIG. 14 shows photographs of single particles trapped in air.

To verify that the conical beams have the desired intensity distributions transversely and longitudinally, beam profiles in the vicinity of the trapping region were measured. FIG. 13 illustrates the light intensity distribution for one of the conical beams, shown in a plane transverse to the axis of the conical beams for the appartus illustrated in FIG. 11, which were measured by the inventors.

The images in FIG. 13 were obtained by directly measuring the beam with a charge coupled device (CCD) when the laser was at a very low power. These images indicate that the beam can be focused to a spot, with full-width at half-maximum (FWHM) around 50 µm (see top right). This spot provides the closed end along the axis of the biconical region. The beam profile exhibits relatively little azimuthal variation in intensity (angular variation around the axis). The thickness of the ring is about 100 µm FWHM around the ring. The intensity near the axis, away from the focal region, is low relative to the intensity of the ring (see bottom part), but is not so low that it cannot generate a measurable Raman emission. This ring is a slice through the high-intensity surface that forms the hollow biconical region. When originally formed by the axicon setup, the hollow beams have a series of concentric rings, with rings further from the axis having lower intensities. Here the beam is spatially filtered to allow only the strongest ring to enter the aperture of the MOs. The total length of the round trip in the triangular trapping path is adjusted so that the weaker rings that are further from the optical axis are blocked by the apertures of MOs. This filtering of the beam is designed to reduce unnecessary interferences also.

Using the system shown in FIG. 11, the inventors were able to trap individual micron-sized particles or aggregates of particles of Johnson grass smut spores (one example of a fungal spore), riboflavin, and powders of carbon black, nigrosin, and carbon nanotubes in the open air for times up to hours. The particles were aerosolized by placing them on a microscope slide set under the trapping region, and blowing them into the air either with turbulent air flows from an ultrasonic needle, or with a tiny puff from a can of compressed air. Once the aerosolized particles entered into the trapping region, many particles moved rapidly toward the trap center and competed for a stable position. Typically, only one trapped particle or agglomerate remained after a short time (e.g., seconds). Occasionally, two or three particles were trapped near each other, but were not touching. One likely explanation for this is that each of these separated particles had a residual charge of the same sign, which caused them to repel each other and remain separated. If two particles having charges with opposite sign were trapped, they would probably agglomerate with each other. The elastic scattering light from these particles is strong enough to be visible to the naked eye. For the embodiment shown in FIG. 11, the AOM 440 deflects the beam when on, with the result that there to be no trapping beam, and so particles can enter the sample volume. When the AOM off, it passes the beam so the particles in the trapping volume are trapped, but other particles are not allowed to enter the trap. Also, for a preferred embodiment shown in FIG. 11, the spectrograph 413 may employ an acoustooptic modulator (AOM), also known as an acoustooptic tunable filter (AOTF) to rapidly scan over the wavelengths for measuring the Raman spectrum. In a similar embodiment, a liquid crystal tunable filter may be used to obtain the Raman spectrum.

Further as to FIG. 11, particles are carried by an air flow that moves in the direction into the page (plane of the page) through the sample volume which is near the intersection of the focal points of MO1, MO2 and MO3. FIG. 11 further includes a "trapping region" 415 which is shown in the inset to FIG. 11. FIG. 14 shows photographs of single particles trapped in air which were measured by the inventors. The top photograph in the figure shows a single particle trapped in air by photophoretic forces, as captured by a video camera. Microscope objectives (MOs) are visible, as are the glass cover slips used to protect the MOs from particles and to reduce air currents in the trapping region. MO3 was used to image the fiber and particles in the lower part of this figure. The three bottom photographs in the figure show the images recorded by the CCD for a 100-μm diameter fiber used for aligning the system (left panel), and the three trapped particles (with diameters around 5 μm, 20 μm, 35 μm, respectively) in the panels to the right. Smaller (~2 μm) and larger (~100 μm) particles have also been trapped.

Intitial experiments conductored by the inventors used carbon nano-foam or agglomerates of carbon nanoparticles for "test" particles for photophoretic trapping because of their low-bulk density (2-20 mg/$cm^3$) and very low-thermal conductivity (0.0266 W/mK). The low thermal conductivity helps the carbon nano-foam agglomerate particles to maintain a highly asymmetric surface temperature, which allows them to be trapped using laser powers as low as 0.3 mW. Experimental results, though, showed that solid particles with a much higher density and thermal conductivity than the carbon nano-foam or agglomerates can be readily captured and steadily trapped in air for long times (up to hrs) with sufficient laser power (30 mW or above). The thermal conductivity for carbon black is 6~174 W/mK, which is at least 100 to 1000 times higher than the carbon nano-foam. Agglomerates of carbon nanotubes, which have an even higher thermal conductivity (200~6000 W/mK), were also readily trapped. No thermal conductivity data was found for nigrosin, Johnson grass smut spores, or riboflavin. Higher laser powers (30 mW or higher) were required to capture and trap particles of riboflavin and Johnson grass smut spores. The absorption at 488 nm is probably lower for the smut spores and riboflavin than for the samples that are mostly elemental carbon.

The higher the laser power, the more easily particles can be trapped. The highest power used was 100 mW. Once a particle is trapped, it can remain trapped while the laser power is gradually decreased to some lower limit. The lowest power that was found to be sufficient to hold a carbon black particle for seconds was 1 mW (after it was initially captured with 20 mW).

Usually, no movement of the trapped particle occurs, as monitored by the CCD. Occasionally, a trapped particle leaves the trap. Other times, a trapped particle may drift away from the trapping position, and then bounce back quickly from the beam at the surface of the bicone, and stop where it was trapped previously. These movements often appear correlated with motion of persons in the room, which may increase the turbulent air currents. The drag force on small particles in air can be large, easily exceeding the gravitational force. This sensitivity to movement of persons suggests that particles could be trapped with even lower laser powers for long times in an air-tight chamber with or without a uniform, laminar airflow.

Figures 15A, 15B, 15C:
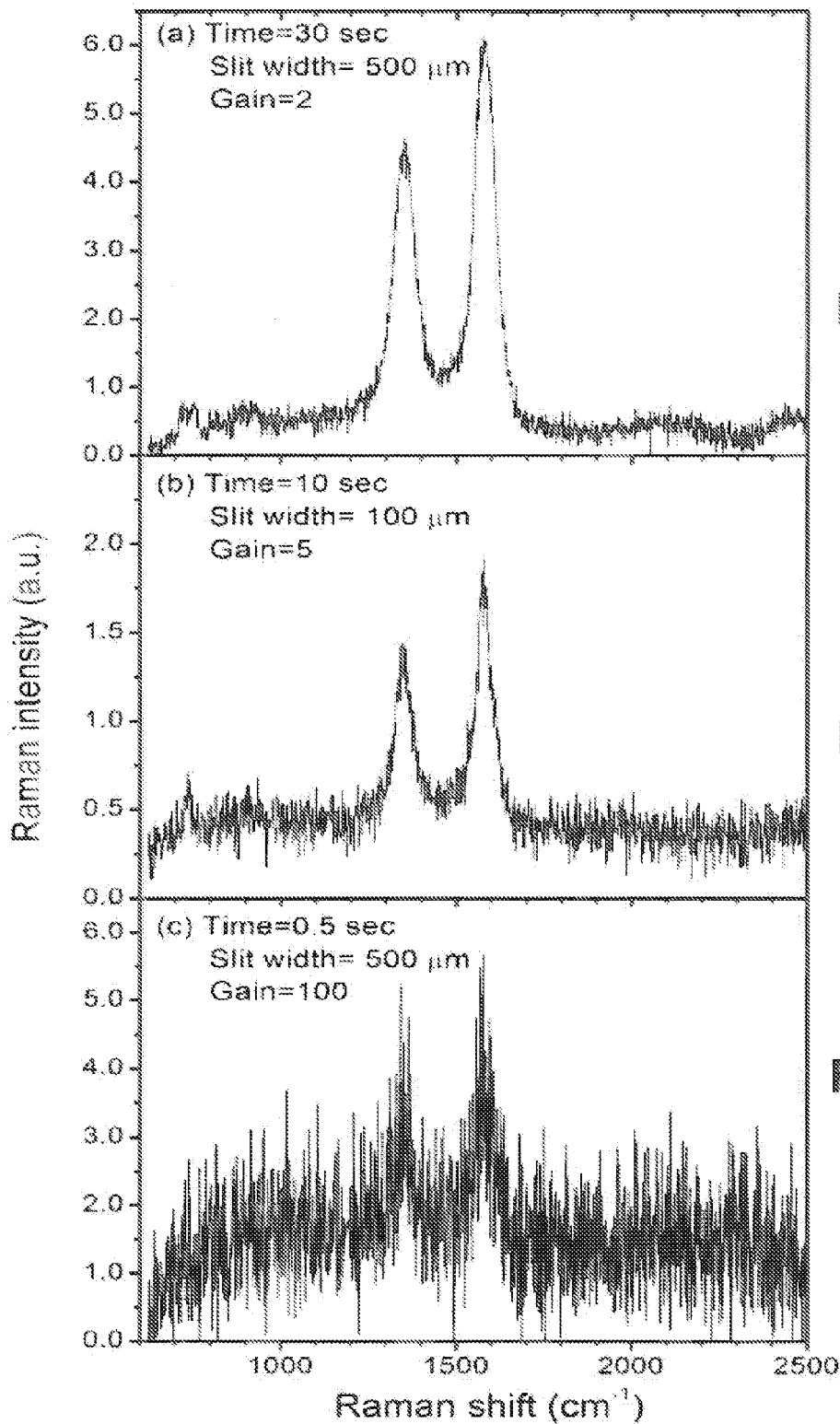
FIGS. 15A-C show the Raman scattering signal of a particle measured using different data acquisition conditions. More particularly.

FIGS. 15A, 15B, and 15C show the Raman scattering signal from a single trapped aggregate (approximately 20 μm diameter) of multi-walled carbon nanotubes (MWCNTs) measured using different data acquisition conditions using the preferred embodiment system illustrated in FIG. 11 (but without the AOM 440). The spectra were obtained using different data acquisition times (30 s, 10 s and 0.5 s), gains (2, 5, and 100) of the EMCCD, and slit widths (500 μm, 100 μm, and 500 μm) of the spectrograph. The 488-nm laser power here was 50 mW. The MWCNTs have an outside diameter less than 7 nm, an inside diameter of approximately 2-5 nm, and a length of approximately 10-30 μm (US Research Nanomaterials, Inc). The Raman signal is excited by the 488-nm beam that also traps the particle.

The spectrograph in FIG. 15A has the largest signal/noise (S/N) (30 s; gain×time=60); the spectrograph in FIG. 15B has the next largest S/N ratio (10 s; gain×time=50); and the spectrographs in FIG. 15C has the smallest S/N (0.5 s; gain×time=50). Even though the width of the entrance slit for the spectrograph in FIG. 16(b) is 100 μm, i.e., ⅕th of the 500 μm used for those of FIGS. 15A and 15C, the S/N in FIG. 15B is larger than in FIG. 15C. The narrow slit width for the spectrograph in FIG. 15B also improves the spectral resolution.

Raman spectra from individual bacterial spores or cells held a using a conventional tweezers trap can be measured with adequate S/N when the particle is illuminated with intensities in the range of 1 MW/cm$^2$ for times of 16 to 60 seconds. These times and large intensities are required because of: a) the extremely small cross sections for Raman scattering from bacteria excited in the near-IR; b) the spread of the Raman emission over a broad range of vibrational frequencies, resulting from the many different molecular species in biological cells; c) the desire to minimize photodamage; and, d) the small sizes of the single bacteria studied (approximately 0.8 to 2 μm diameter for equivalent volume spheres). A comparison of such measurements with measurement made using conventional tweezers traps for the absorbing carbon particles illustrated in the figures is as follows. The illumination intensity on the particles in FIG. 15 was estimated to be roughly 10$^4$ times smaller than that used for Raman measurements of bacteria trapped with laser tweezers as reported by D. Chen, S. S. Huang, and Y. Q. Li, "Real-time detection of kinetic germination and heterogeneity of single *Bacillus* spores by laser tweezers Raman spectroscopy," Anal. Chem. 78(19), 6936-6941 (2006); and C. Xie and Y. Q. Li, "Confocal micro-Raman spectroscopy of single biological cells using optical trapping and shifted excitation difference techniques," J. Appl. Phys. 93(5), 2982-2986 (2003), both herein incorporated by reference. The intensity illuminating the particles in FIGS. 15A-15C is estimated to be roughly 100 W/cm$^2$ (when the laser power was 30 mW). The intensity was kept low partly because of our interest in a system that does not require high power. When the laser power was increased to 100 mW, the trap was more able to catch less-absorbing particles and it would generate stronger Raman signals, if they had been measured. The laser intensity was also kept low partly to avoid overheating or photodegrading the particles. However, the inventors did not notice evidence of overheating or of photodegradation even when the laser power was increased to 100 W/cm$^2$. Using the analysis reported by J. R. Finke et al, "Measurement of the emissivity of small particles at elevated temperatures," Opt. Eng. 27, 684-690 (1988)), herein incorporated by reference, an increase in equilibrium temperature of 84° C. was estimated for a cw 30-mW beam illuminating a solid 20-μm diameter particle that absorbs all the light impinging directly on it (i.e., for an absorption efficiency of 1.0). A typical diameter of many atmospheric particles to be measured is approximately 2 μm. The increase in equilibrium temperature for a highly absorbing 2 μm particle was estimated to be 8° C., for 30-mW illumination. Increasing the illumination intensity on the particle could reduce the acquisition times required for Raman spectra. This increase could be achieved by increasing the laser power. It could also be achieved by adjusting the optics to increase the intensity at the center of the beam so long as that the trapping intensity forming the biconical trap was also increased. Efficient trapping does not require that the intensity at the center of the trap be very small. Trapping requires that intensity barrier preventing the particles from leaving the trap be sufficiently high above the intensity (whatever it is) at the intensity minimum of the trapping region.

For photophoretic trapping, the laser wavelength should be absorbed well by at least one of the species of molecules in the particle (a species that comprises a significant percentage of the mass of the particle, e.g., 0.5%, depending upon the particle mass). Therefore, it is likely that at least one of the species in a photophoretically trapped particle will exhibit a resonantly enhanced Raman cross section. Resonance Raman cross sections can be orders of magnitude larger than those measured far from resonance. In laser-tweezers trapping the excitation wavelength for the Raman emission cannot be near a resonance of a molecule that contributes a significant fraction of the mass of the particle. If the wavelength were near an absorption resonance, then the photophoretic forces would dominate over the radiation pressure forces and push the particle out of from trap.

Excitation of Raman emission at wavelengths below about 248 nm is particularly useful for measurements of bioaerosols because: a) the fluorescence is separated from the Raman spectrum; b) the Raman cross section is relatively large (it increases as frequency to the 4$^{th}$ power); c) the absorption of amino acids and nucleic acids are relatively strong at wavelengths in the 220-nm to 248-nm range; and, d) there is some resonance enhancement of the Raman spectra. Therefore, Raman spectra can be measured relatively quickly. On the other hand, conventional radiation pressure traps cannot be used for bioaerosols at these wavelengths because light at these wavelengths is absorbed well and so photophoretic forces strongly dominate over radiation pressure forces for the biological materials of interest.

In FIGS. 15A-C the diameters of the MWCNT particles have diameters roughly 20 times larger than the diameters of the bacterial spores measured in the near-IR. The absorption by these 20-μm diameter MWCNT particles would be roughly 400 times larger than a 1 μm MWCNT particle. Although Raman cross sections of selected individual carbon nanotubes, excited near resonance with an ideal orientation, can be as large as $10^{-22}$ cm$^2$/sr, it is not clear how such a number applies to the case studied here, where there is extensive a dispersion in nanotube diameters, orientations, and numbers of walls.

The Raman signal will be generated near the surface of a MWCNT particle because each particle is large and highly absorbing. In the transparent bacterial particles studied in tweezers traps where the Raman emission is excited by wavelengths in the near IR, molecules throughout the volume should be able to contribute to the signal.

A high fraction of the Raman emitted by a nanotube structure (but not necessarily by the particle composed of many nanotubes), for instance, will tend to be absorbed before it is able to exit the particle. This absorption should occur because the MWCNT material is highly absorbing at the Raman emission wavelengths. This reabsorption of emission would not be significant in the case of the low-absorbing particles studied with laser tweezers in the near IR. This reabsorption of emission would not occur for materials where the absorption of the excitation wavelength is high (needed for photophoretic trapping with excitation at the trapping wavelength), but where the absorption of light at the wavelengths of the Raman emission is relatively low.

Illumination of particles using wavelengths of light in the 220 nm to 248 nm range has several advantages for both measuring Raman and for trapping biological aerosols. One difficulty in measuring Raman spectra from biological materials is that when these biomaterials are excited at wavelengths from about 250 nm to 650 nm, the fluorescence can overlap the Raman signal and can swamp the Raman signal because it typically much larger than the Raman emission.

To address this problem, in one approach the fluorescence is first photobleached and the Raman spectrum is measured as reported by K. S. Kalasinsky et al, "Raman chemical imaging spectroscopy reagentless detection and identification of pathogens: signature development and valuation," Anal. Chem. 79, 2658-2673 (2007) & J. Guicheteau et al, "Bacterial mixture identification using Raman and surface-enhanced Raman chemical imaging," J. Raman Spectroscopy. 41, 1632-1637 (2010), herein incorporated by reference. This approach works well, for instance, for measuring Raman of particles collected on a surface. However, because the required photobleaching times are usually longer than 1 minute, it may not suitable for the continuously sampling.

Another approach is to reduce the fluorescence-Raman overlap by illuminating the particles with wavelengths shorter than about 248 nm. At these wavelengths, the fluorescence from biological materials is shifted sufficiently far from the laser wavelength, and the Raman emission stays sufficiently close to the laser wavelength, that the Raman spectra are measurable with very little fluorescence interference. As a result, photobleaching of the fluorescence is not required for measurements of good quality Raman spectra, and so spectra of bioaerosols can be obtained without a need to photobleach.

Other benefits of exciting the Raman emission at wavelengths below 248 nm are: a) the Raman cross sections increase by $(1/\lambda)^4$, (where $\lambda$ is the excitation wavelength), and that gives a factor of 81 increase in the Raman emission intensity when the excitation wavelength is decreased from 732 nm to 244 nm (a factor of 3 reduction in wavelength); b) many of the biological molecules of interest absorb strongly at these wavelengths below 248 nm, and so the Raman emission can be resonantly enhanced; and, c) the particles should be easier to trap photophoretically at wavelengths below 248 nm because they are more absorbing.

For embodiments that use wavelengths shorter than 248 nm, photophoretic bottle beam traps that use relatively few optical elements (e.g., a single lens, or a single aperture, or a single phase plate) may be particularly desirable because of the cost of certain optical elements (e.g., beam splitters, axicons, waveplates, etc.) at these short wavelengths is significant and because the absorption of the light by these elements can be significant.

One or more embodiments of the invention may be useful in the pharmaceutical industry, particularly in relation to drugs which are delivered as aerosols (which are inhaled). Improvements are needed regarding the inhalation dosages achieved, etc. The system and methods described here may measure both the drug composition and the particle size. Additionally, they may be used in on-line monitoring, and in research and development. And, one or more embodiments of the invention may be useful for researchers studying atmospheric and indoor aerosols, including aerosol compositions, responses to pollutants and sunlight, and the effects of atmospheric aerosol on global climate (via absorption, scattering and acting as cloud condensation nuclei).

In some embodiments, the system may be deployed in hospitals, clinics, emergency rooms, public places (shopping malls, train and bus stations, airports, public transportation, sports arenas, etc.), government buildings, or other locations for monitoring air. In addition, the systems may be deployed in a military context, for instance, at a military installation (e.g. base), in a vehicle, on the battlefield, etc. These systems can rapidly detect or characterize particles in air, and help save lives in case of a biological agent attack.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present disclosure and its practical applications, and to describe the actual partial implementation in the laboratory of the system which was assembled using a combination of existing equipment and equipment that could be readily obtained by the inventors, to thereby enable others skilled in the art to best utilize the invention and various embodiments with various modifications as may be suited to the particular use contemplated.

While the foregoing is directed to embodiments of the present invention, other and further embodiments of the invention may be devised without departing from the basic scope thereof, and the scope thereof is determined by the claims that follow.

We claim:
1. A system for continuously sampling particles from air comprising:
    an airflow system configured to generate an airflow by continuously drawing ambient air including airborne particles into the system and expelling airborne particles from the system;
    a photophoretic trap that uses photophoretic forces of a laser beam to trap and hold in the airflow one or more light-absorbing airborne particles from the drawn air;
    a measurement device comprising a Raman detecting system configured to measure Raman spectra and optionally one or more additional systems configured to mea- sure one or more other properties of the trapped one or more light-absorbing airborne particles while the airflow passes; and a controller configured to repeatedly trap, measure and release into the airflow one or more light-absorbing airborne particles.

2. The system of claim 1, wherein the photophoretic trap is configured to trap and hold only about one light-absorbing particle at any one time.

3. The system of claim 1, wherein one laser is used to trap the light-absorbing particle and to generate one or more emissions of, and/or elastic scattering by, the trapped one or more light-absorbing airborne particles.

4. The system of claim 1, further comprising: a particle detector configured to detect an airborne particle approaching and/or within the photophoretic trap.

5. The system of claim 1, further comprising: at least one separate laser configured to excite emissions of the trapped one or more light-absorbing airborne particles.

6. The system of claim 1, wherein the measurement device comprises the one or more additional systems further configured to measure one or more of: laser-induced breakdown emission in one or more wavelength bands, laser-induced breakdown spectra, spark-induced breakdown emission in one or more wavelength bands, spark-induced breakdown spectra, fluorescence in one or more wavelength bands, fluorescence spectra, multi-photon excited fluorescence, thermal emission at one or more wavelengths, thermal emission spectra, or light scattering over one or more angles.

7. The system of claim 1, further comprising a particle analyzer configured to determine, from the measured property, a parameter related to particle shape, size, refractive index, absorption, or any combination thereof of the trapped one or more light-absorbing airborne particles.

8. The system of claim 7, wherein the particle analyzer is configured to execute an algorithm which identifies or classifies particles into different categories based on their measured properties.

9. The system of claim 8, wherein the algorithm used to identify or classify particles further includes other information regarding the sampling site, or the atmospheric conditions, or the time of year, or the calculated trajectory of the air mass reaching the air sampler.

10. The system of claim 1, further comprising: a particle sorter configured to physically sort, and optionally store, particles based on their measured properties.

11. The system of claim 1, wherein the controller is configured to generate signals to:

trap and hold one or more light-absorbing airborne particles in the photophoretic trap;

determine whether an airborne light-absorbing particle has been trapped in the photophoretic trap;

measure Raman spectra and optionally one or more other properties of the one or more trapped light-absorbing airborne particles; and release the one or more trapped light-absorbing airborne particles.

12. The system of claim 11, further comprising: a particle detector configured to detect an airborne particle approaching and/or within the photophoretic trap, wherein the controller is configured to generate a signal causing the measuring device to measure the one of more properties of the one or more trapped light-absorbing airborne particles based on a signal received from the particle detection device in response to detecting a particle.

13. The system of claim 11, further comprising: a particle detector configured to detect an airborne particle approaching and/or within the photophoretic trap, wherein the controller is configured to generate a signal causing the photophoretic trap to trap the one or more trapped airborne particles based on a signal received from the particle detection device in response to detecting a particle.

14. The system of claim 4, wherein the particle detector comprises two different-wavelength crossed-beam diode lasers with corresponding photodetectors, each of said photodetectors including an optical filter that passes the wavelength of the diode laser it detects and blocks the light from the other diode laser and light at any other wavelengths that would interfere.

15. The system of claim 1, wherein the controller is configured to modulate the intensity or spatial variation of the laser beam that traps the particles.

16. The system of claim 1, further comprising a blocking element configured to be actuated so as to block the laser trapping beam from reaching the photophoretic trap.

17. The system of claim 1, further comprising: a particle concentrator configured to concentrate particles and direct them to the photophoretic trap.

18. The system of claim 1, wherein the photophoretic trap is generated using a single Gaussian laser beam focused with a simple lens having two spherical surfaces, or other optical system having significant aberration.

19. The system of claim 1, wherein the photophoretic trap is generated using a single laser beam of elliptical cross-section focused with a simple lens having two spherical surfaces, or other optical system having significant aberration.

20. A method for continuously sampling particles from air, comprising:

continuously directing an airflow including airborne particles toward a photophoretic trap located in the airflow that uses photophoretic forces of a laser beam to trap one or more of the light-absorbing airborne particles;

detecting an light-absorbing airborne particle in the air approaching and/or within the photophoretic trap;

trapping one or more light-absorbing airborne particles in the photophoretic trap;

measuring Raman spectra and optionally another property of the trapped one or more light-absorbing airborne particles; and releasing the trapped one or more light-absorbing airborne particles to move in the airflow.

21. The method of claim 20, further comprising: determining from the measured property a parameter related to particle shape, size, refractive index, absorption, or any combination thereof of the trapped one or more light-absorbing airborne particles.

22. The method of claim 20, further comprising:

selecting another measurement for a property of the trapped one or more light-absorbing airborne particles.

23. The method of claim 20 further comprising: activating a sorting and collecting subsystem which collects particle for further study when the measurements and parameters of the trapped one or more light-absorbing airborne particles satisfy one or more criteria or satisfy an algorithm based on these measurements, parameters, and any other information the algorithm uses.

24. The system of claim 1, wherein the flow rate of the airflow is more than 1 cm/s and less than 1 m/s.

25. The system of claim 1, wherein acquisition times for Raman measurement is on the order of milliseconds to seconds.

26. The system of claim 1, wherein the Raman spectral measurements comprise one or more of: Raman scattering, Raman spectroscopy, Resonance Raman spectroscopy, Coherent anti-stokes Raman scattering (CARS), and surface enhanced Raman scattering (SERS).

* * * * *